(12) United States Patent
Ruben et al.

(10) Patent No.: US 10,098,589 B2
(45) Date of Patent: Oct. 16, 2018

(54) SEALED PACKAGE AND METHOD OF FORMING SAME

(71) Applicant: Medtronic, Inc., Minneapolis, MN (US)

(72) Inventors: David A Ruben, Mesa, AZ (US); Craig L Schmidt, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/359,974

(22) Filed: Nov. 23, 2016

(65) Prior Publication Data

US 2017/0172505 A1    Jun. 22, 2017

Related U.S. Application Data

(60) Provisional application No. 62/270,119, filed on Dec. 21, 2015.

(51) Int. Cl.
*H05K 5/06* (2006.01)
*A61B 5/00* (2006.01)
(Continued)

(52) U.S. Cl.
CPC .......... *A61B 5/686* (2013.01); *A61B 5/0245* (2013.01); *A61N 1/05* (2013.01); *H05K 1/115* (2013.01);
(Continued)

(58) Field of Classification Search
CPC ...... H05K 1/115; H05K 1/183; H05K 3/0017; H05K 3/32; H05K 3/4038; H05K 5/0247;
(Continued)

(56) References Cited

U.S. PATENT DOCUMENTS

| 4,605,007 A | 8/1986 | Heraly |
| 4,700,473 A | 10/1987 | Freyman et al. |

(Continued)

FOREIGN PATENT DOCUMENTS

| EP | 0232935 A1 | 8/1987 |
| EP | 1864784 A1 | 12/2007 |

(Continued)

OTHER PUBLICATIONS (PCT/US2016/063859) PCT Notification of Transmittal of the International Search Report and the Written Opinion of the International Searching Authority, dated Feb. 20, 2017, 10 pages.

(Continued)

*Primary Examiner* — Angel R Estrada

(57) ABSTRACT

Various embodiments of a sealed package and a method of forming such package are disclosed. The package can include a non-conductive substrate that includes a cavity disposed in a first major surface. A cover layer can be disposed over the cavity and attached to the first major surface of the non-conductive substrate to form a sealed enclosure. The sealed package can also include a feedthrough that includes a via between a recessed surface of the cavity and a second major surface of the substrate, and a conductive material disposed in the via. An external contact can be disposed over the via on the second major surface of the non-conductive substrate, where the external contact is electrically connected to the conductive material disposed in the via. The sealed package can also include an electronic device disposed within the sealed enclosure that is electrically connected to the external contact.

20 Claims, 9 Drawing Sheets

(51) Int. Cl.
  *H05K 5/02* (2006.01)
  *H05K 1/18* (2006.01)
  *H05K 1/11* (2006.01)
  *H05K 5/03* (2006.01)
  *H05K 3/40* (2006.01)
  *H05K 3/32* (2006.01)
  *H05K 3/00* (2006.01)
  *A61B 5/0245* (2006.01)
  *A61N 1/05* (2006.01)

(52) U.S. Cl.
  CPC .......... *H05K 1/183* (2013.01); *H05K 3/0017* (2013.01); *H05K 3/32* (2013.01); *H05K 3/4038* (2013.01); *H05K 5/0247* (2013.01); *H05K 5/03* (2013.01); *H05K 5/066* (2013.01); *H05K 5/069* (2013.01); *H05K 2201/09036* (2013.01)

(58) Field of Classification Search
  CPC .......... H05K 5/03; H05K 5/066; H05K 5/069; H05K 2201/09036; A61B 5/686; A61B 5/0245; A61N 1/05
  USPC .................. 174/50.5, 50.51, 50.52, 520, 535
  See application file for complete search history.

(56) References Cited

U.S. PATENT DOCUMENTS

| | | | |
|---|---|---|---|
| 4,785,827 A | 11/1988 | Fischer | |
| 4,810,318 A | 3/1989 | Haisma et al. | |
| 5,054,683 A | 10/1991 | Haisma et al. | |
| 5,315,486 A | 5/1994 | Fillion | |
| 5,489,321 A | 2/1996 | Tracy et al. | |
| 5,647,932 A | 7/1997 | Taguchi et al. | |
| 5,693,111 A | 12/1997 | Kadowaki et al. | |
| 5,814,091 A | 9/1998 | Dahlberg et al. | |
| 6,477,901 B1 | 11/2002 | Tadigadapa et al. | |
| 6,555,025 B1 | 4/2003 | Krupetsky et al. | |
| 6,717,100 B2 | 4/2004 | Ruben | |
| 6,762,072 B2 | 7/2004 | Lutz | |
| 6,822,326 B2 | 11/2004 | Enquist et al. | |
| 6,963,780 B2 | 11/2005 | Ruben et al. | |
| 7,078,726 B2 | 7/2006 | Pichler et al. | |
| 7,153,775 B2 | 12/2006 | Geusic et al. | |
| 7,288,847 B2 | 10/2007 | Ruben et al. | |
| 7,417,307 B2 | 8/2008 | Haluzak et al. | |
| 7,540,934 B2 | 6/2009 | Hofmann et al. | |
| 7,647,110 B2 | 1/2010 | Hörnfeldt et al. | |
| 7,794,866 B2 | 9/2010 | Youker et al. | |
| 7,822,482 B2 | 10/2010 | Gerber | |
| 7,872,208 B2 | 1/2011 | Ruben et al. | |
| 7,902,851 B2 | 3/2011 | Fenner et al. | |
| 8,125,146 B2 | 2/2012 | Park | |
| 8,231,998 B2 | 7/2012 | Sastry et al. | |
| 8,233,986 B2 | 7/2012 | Deininger et al. | |
| 8,295,929 B2 | 10/2012 | Fang et al. | |
| 8,448,468 B2 | 5/2013 | Pastel et al. | |
| 8,473,056 B2 | 6/2013 | Engmark et al. | |
| 8,626,310 B2 | 1/2014 | Barror et al. | |
| 8,644,936 B2 | 2/2014 | Iyer et al. | |
| 8,666,505 B2 | 3/2014 | O'Brien et al. | |
| 8,796,109 B2 | 8/2014 | Ruben et al. | |
| 9,120,287 B2 | 9/2015 | Ruben et al. | |
| 9,171,121 B2 | 10/2015 | Danzl et al. | |
| 2002/0066940 A1 | 6/2002 | Ruben | |
| 2002/0115920 A1 | 8/2002 | Rich et al. | |
| 2003/0018364 A1 | 1/2003 | Belden et al. | |
| 2004/0012083 A1 | 1/2004 | Farrell et al. | |
| 2004/0056350 A1 | 3/2004 | Ruben | |
| 2004/0082145 A1 | 4/2004 | Reichenbach et al. | |
| 2005/0007718 A1 | 1/2005 | Stevenson et al. | |
| 2005/0151151 A1 | 7/2005 | Hawtof et al. | |
| 2005/0284815 A1 | 12/2005 | Sparks et al. | |
| 2006/0247714 A1 | 11/2006 | Taylor et al. | |
| 2006/0259093 A1 | 11/2006 | Stevenson et al. | |
| 2006/0267167 A1 | 11/2006 | McCain | |
| 2007/0043399 A1 | 2/2007 | Stevenson et al. | |
| 2007/0160748 A1 | 7/2007 | Schugt et al. | |
| 2007/0170839 A1 | 7/2007 | Choi et al. | |
| 2008/0102096 A1 | 5/2008 | Molin et al. | |
| 2008/0140148 A1 | 6/2008 | Rogier | |
| 2008/0183225 A1 | 7/2008 | Adamski et al. | |
| 2008/0265423 A1 | 10/2008 | Ruben | |
| 2008/0269623 A1 | 10/2008 | Ruben | |
| 2009/0059468 A1 | 3/2009 | Iyer | |
| 2009/0308169 A1 | 12/2009 | Mothilal et al. | |
| 2010/0009150 A1 | 1/2010 | Mitooka et al. | |
| 2010/0262208 A1 | 10/2010 | Parker | |
| 2010/0263794 A1 | 10/2010 | George et al. | |
| 2010/0304151 A1 | 12/2010 | Tuennermann et al. | |
| 2010/0314149 A1 | 12/2010 | Gerrish et al. | |
| 2011/0190833 A1 | 8/2011 | Ries et al. | |
| 2011/0270099 A1 | 11/2011 | Ruben et al. | |
| 2012/0100318 A1 | 4/2012 | Danzl et al. | |
| 2012/0101540 A1 | 4/2012 | O'Brien et al. | |
| 2012/0108954 A1 | 5/2012 | Schulhauser et al. | |
| 2012/0197155 A1 | 8/2012 | Mattes et al. | |
| 2012/0303105 A1 | 11/2012 | Askarinya et al. | |
| 2012/0309237 A1 | 12/2012 | Marzano et al. | |
| 2013/0035733 A1 | 2/2013 | Breyen et al. | |
| 2013/0196214 A1 | 8/2013 | Scott et al. | |
| 2013/0337313 A1 | 12/2013 | Askarinya et al. | |
| 2015/0101841 A1 | 4/2015 | Ruben et al. | |
| 2015/0250386 A1 | 9/2015 | James et al. | |
| 2016/0184593 A1 | 6/2016 | Ruben | |
| 2016/0185081 A1 | 6/2016 | Sandlin et al. | |
| 2016/0190052 A1 | 6/2016 | Ruben et al. | |
| 2016/0192524 A1 | 6/2016 | Ruben | |

FOREIGN PATENT DOCUMENTS

| | | |
|---|---|---|
| WO | 00/65682 | 11/2000 |
| WO | WO 2010/117382 A1 | 10/2010 |
| WO | WO 2016/106269 A1 | 6/2016 |
| WO | WO 2016/106272 A1 | 6/2016 |
| WO | WO 2016/106274 A1 | 6/2016 |
| WO | WO 2016/106323 A1 | 6/2016 |

OTHER PUBLICATIONS

Brown, "Precision Laser Welding of Clear Thermoplastics Without Additives," Medical Design Technology, Aug. 5, 2013, 7 pages. Located on the World Wide Web at http://www.mdtmag.com/articles/2013/08/precision-laser-welding-clear-thermoplastics-without-additives.

Gillner et al., "Laser Bonding of Micro Optical Components," Proceedings of SPIE, vol. 4941, pp. 112-120, Oct. 2003.

International Preliminary Report on Patentability for corresponding patent application No. PCT/US2011/034371, dated Jul. 4, 2013, 7 pages.

International Search Report and Written Opinion of international application No. PCT/US2011/034371, dated Jun. 24, 2011, 11 pp.

Park, "Characterization of transmission laser bonding (TLB) technique for microsystem packaging," Arizona State University, May 2006 (135 pp.).

Sari et al., "Applications of laser transmission processes for the joining of plastics, silicon and glass micro parts," Microsyst Technol (2008) 14: 1879-1886, published online Jul. 18, 2008.

Theppakuttai et al., "Localized Laser Transmission Bonding for Microsystem Fabrication and Packaging," Journal of Manufacturing Processes, vol. 6, No. 1, 2004 (8 pp.).

Wiemer et al., "Developments trends in the field of wafer bonding technologies," 214th ECS Meeting, Abstract #2229, Oct. 12-Oct. 17, 2008, Honolulu, HI (1 p.).

Wild et al. "Locally selective bonding of silicon and glass with laser," Sensors and Actuators A: Physical, vol. 93, Issue 1, Aug. 25, 2001, p. 63-69.

Witte et al., "Laser joining of glass with silicon," Proceedings of SPIE, vol. 4637, Jan. 21, 2002, pp. 487-495.

(56) References Cited

OTHER PUBLICATIONS

Claims from U.S. Appl. No. 14/966,181, filed Dec. 11, 2015.
Claims from U.S. Appl. No. 14/966,101, filed Dec. 11, 2015.
(PCT/US2015/067262) PCT Notification of Transmittal of the International Search Report and the Written Opinion of the International Searching Authority, dated Apr. 14, 2016, 11 pages.
(PCT/US2015/067260) PCT Notification of Transmittal of the International Search Report and the Written Opinion of the International Searching Authority, dated Apr. 19, 2016, 10 pages.
(PCT/US15/067257) PCT Notification of Transmittal of the International Search Report and the Written Opinion of the International Searching Authority, dated Mar. 17, 2016, 10 pages.

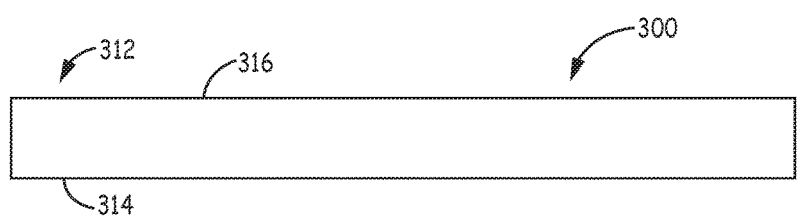
FIG. 8A
FIG. 8B
FIG. 8C
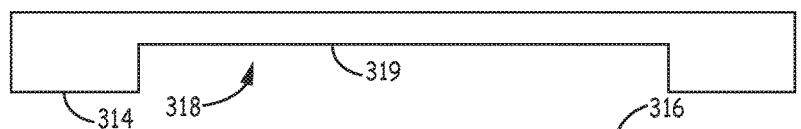
FIG. 8D
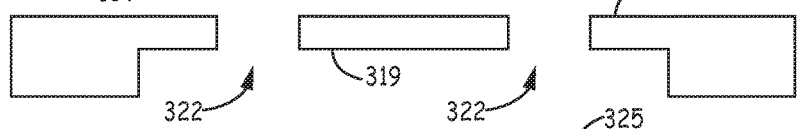
FIG. 8E
FIG. 8F
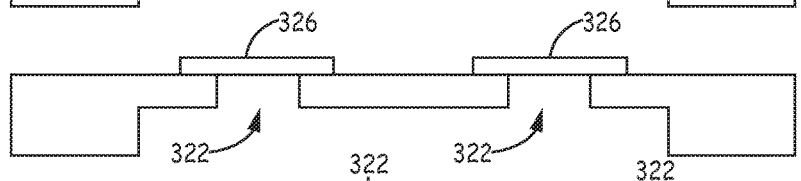
FIG. 8G
FIG. 8H
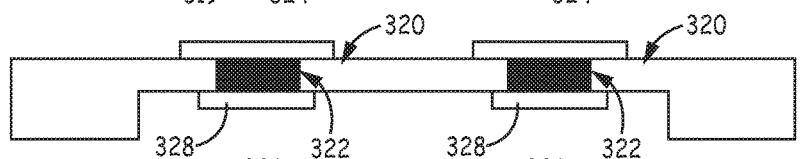
FIG. 8I

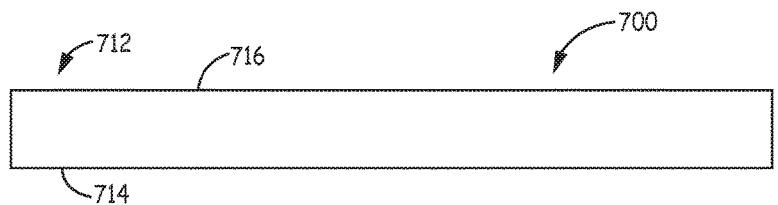
FIG. 13A
FIG. 13B
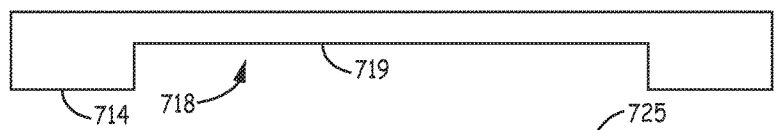
FIG. 13C
FIG. 13D
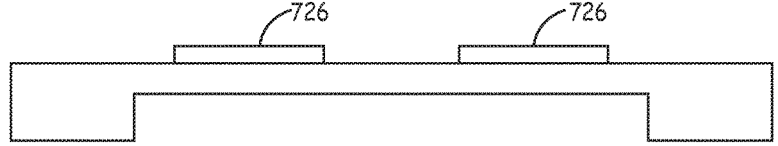
FIG. 13E
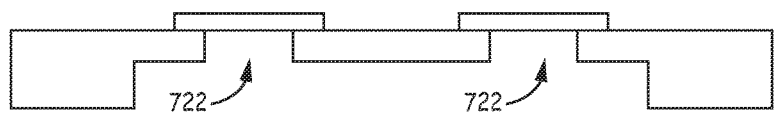
FIG. 13F
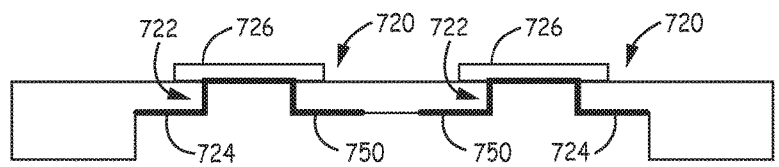
FIG. 13G
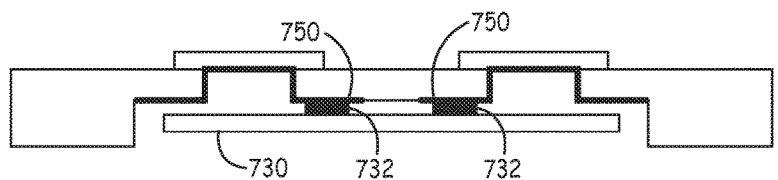
FIG. 13H
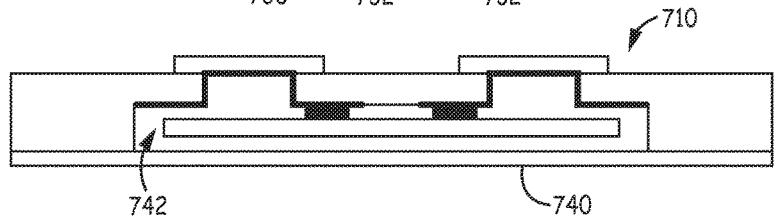

SEALED PACKAGE AND METHOD OF FORMING SAME

CROSS-REFERENCE TO RELATED APPLICATION

This application claims priority to U.S. Provisional Patent Application No. 62/270,119, filed Dec. 21, 2015, which is incorporated herein by reference.

BACKGROUND

Various systems require electrical coupling between electrical devices disposed within a hermetically sealed enclosure and external devices. Oftentimes, such electrical coupling needs to withstand various environmental factors such that a conductive pathway or pathways from the external surface to within the enclosure remains stable. For example, implantable medical devices (IMDs), e.g., cardiac pacemakers, defibrillators, neurostimulators and drug pumps, which include electronic circuitry and battery elements, require an enclosure or housing to contain and hermetically seal these elements within a body of a patient. Many of these IMDs include one or more electrical feedthrough assemblies to provide electrical connection between the elements contained within the housing and components of the IMD external to the housing, for example, sensors and/or electrodes and/or lead wires mounted on an exterior surface of the housing, or electrical contacts housed within a connector header, which is mounted on the housing to provide coupling for one or more implantable leads, which typically carry one or more electrodes and/or one or more other types of physiological sensors. A physiological sensor, for example a pressure sensor, incorporated within a body of a lead may also require a hermetically sealed housing to contain electronic circuitry of the sensor and an electrical feedthrough assembly to provide an electrical connection between one or more lead wires, which extend within the implantable lead body, and the contained circuitry.

A feedthrough assembly typically includes one or more feedthrough pins that extend from an interior to an exterior of the housing through a ferrule. Each feedthrough pin is electrically isolated from the ferrule, and, for multipolar assemblies, from one another, by an insulator element, e.g., glass or ceramic, that is mounted within the ferrule and surrounds the feedthrough pin(s). Glass insulators are typically sealed directly to the pin(s) and to the ferrule, e.g., by heating the assembly to a temperature at which the glass wets the pin(s) and ferrule, while ceramic insulators are typically sealed to the pin(s) and to the ferrule by a braze joint. High temperatures are typically required to join corrosion-resistant conductive materials with corrosion-resistant insulative materials.

SUMMARY

In general, the present disclosure provides various embodiments of a sealed package and a method of forming such package. In one or more embodiments, the sealed package can be a hermetically-sealed package. The sealed package can include a non-conductive substrate that includes a cavity disposed in a first major surface. A cover layer can be disposed over the cavity and attached to the first major surface of the non-conductive substrate to form a sealed enclosure. The sealed package can also include a feedthrough that includes a via between a recessed surface of the cavity and a second major surface of the substrate, and a conductive material disposed in the via. An external contact can be disposed over the via on the second major surface of the non-conductive substrate, where the external contact is electrically connected to the conductive material disposed in the via. In one or more embodiments, the external contact can be hermetically sealed to the second major surface of the non-conductive substrate using any suitable technique or combination of techniques, e.g., a laser bond that at least partially surrounds the via can be formed between the external contact and the second major surface of the non-conductive substrate. In one or more embodiments, the sealed package can include an electronic device disposed within the sealed enclosure. The electronic device can include a device contact that is electrically connected to the conductive material disposed in the via such that the electronic device is electrically connected to the external contact.

In one aspect, the present disclosure provides a hermetically-sealed package that includes a non-conductive substrate including a first major surface, a second major surface, and a cavity disposed in the first major surface. The cavity includes a recessed surface. The package also includes a cover layer disposed over the cavity and attached to the first major surface of the non-conductive substrate to form a hermetically-sealed enclosure, and a feedthrough. The feedthrough includes a via between the recessed surface of the cavity and the second major surface of the substrate; a conductive material disposed in the via; and an external contact disposed over the via on the second major surface of the non-conductive substrate. The external contact is electrically connected to the conductive material disposed in the via, and the external contact is hermetically sealed to the second major surface of the non-conductive substrate by a laser bond surrounding the via. The package also includes an electronic device disposed within the hermetically-sealed enclosure, where the electronic device includes a device contact that is electrically connected to the conductive material disposed in the via such that the electronic device is electrically connected to the external contact.

In another aspect, the present disclosure provides a method of forming a hermetically-sealed package. The method includes forming a cavity in a first major surface of a non-conductive substrate; forming a via between a recessed surface of the cavity and a second major surface of the non-conductive substrate; and forming an external contact over the via on the second major surface of the non-conductive substrate. The method further includes disposing conductive material in the via such that the external contact is electrically connected to the conductive material in the via; disposing an electronic device at least partially within the cavity such that a device contact of the electronic device is electrically connected to the conductive material in the via; disposing a cover layer over the cavity; and attaching the cover layer to the first major surface of the non-conductive substrate to form a hermetically-sealed enclosure. The electronic device is disposed within the hermetically-sealed enclosure.

In another aspect, the present disclosure provides a hermetically-sealed package that includes a non-conductive substrate including a first major surface, a second major surface, and a cavity disposed in the first major surface. The cavity includes a recessed surface. The package further includes an internal contact disposed on the recessed surface of the cavity; an electronic device including a device contact electrically connected to the internal contact; and a cover layer disposed over the cavity and attached to the first major surface of the non-conductive substrate to form a hermetically-sealed enclosure. The electronic device is disposed within the hermetically-sealed enclosure.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein:

FIGS. 8A, 8B, 8C, 8D, 8E, 8F, 8G, 8H and 8I are schematic cross-section views of a method of forming a sealed package.

FIGS. 13A, 13B, 13C, 13D, 13E, 13F, 13G and 13H are schematic cross-section views of another method of forming a sealed package.

DETAILED DESCRIPTION

Figure 1:
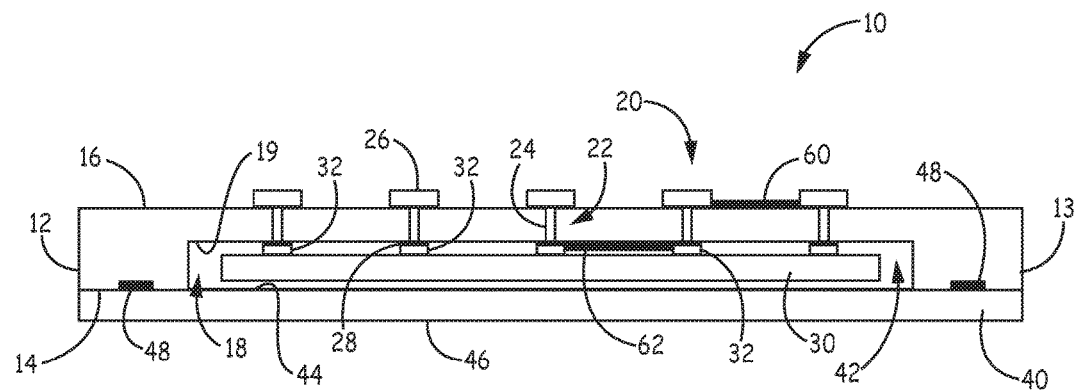
FIG. 1 is a schematic cross-section view of one embodiment of a sealed package.

In general, the present disclosure provides various embodiments of a sealed package and a method of forming such package. In one or more embodiments, the sealed package can be a hermetically-sealed package. The sealed package can include a non-conductive substrate that includes a cavity disposed in a first major surface. A cover layer can be disposed over the cavity and attached to the first major surface of the non-conductive substrate to form a sealed enclosure. The sealed package can also include a feedthrough that includes a via between a recessed surface of the cavity and a second major surface of the substrate, and a conductive material disposed in the via. An external contact can be disposed over the via on the second major surface of the non-conductive substrate, where the external contact is electrically connected to the conductive material disposed in the via. In one or more embodiments, the external contact can be hermetically sealed to the second major surface of the non-conductive substrate using any suitable technique or combination of techniques, e.g., a laser bond that at least partially surrounds the via can be formed between the external contact and the second major surface of the non-conductive substrate. In one or more embodiments, the sealed package can include an electronic device disposed within the sealed enclosure. The electronic device can include a device contact that is electrically connected to the conductive material disposed in the via such that the electronic device is electrically connected to the external contact.

In one or more embodiments, the feedthrough can be formed through the substrate using low temperature techniques that do not require the use of ferrules, glasses, or brazing materials. Further, in one or more embodiments, the feedthrough can be formed without creating unacceptable stresses in the materials used to form the feedthrough that can be caused by the use of high temperature bonding techniques. Further, in one or more embodiments, the external contact of the feedthrough and an optional internal contact electrically coupled to the via can be of sufficient size and thickness to enable laser, resistance, or other welding and joining techniques to be utilized to electrically couple conductors and/or electronic devices to the contacts. In addition, in one or more embodiments, the disclosed low temperature processing techniques can also allow for internal metallization such as Ti/Ni/Au directly on a non-conductive substrate. This can, in one or more embodiments, facilitate the disposition of various electronic devices directly onto the substrate, e.g., integrated circuits, or discrete circuit components such as filtering capacitors, diodes, resistors, etc., as is further described herein.

FIGS. 1-5 are various schematic views of one embodiment of a sealed package 10. The package 10 includes a substrate 12 that has a first major surface 14 and a second major surface 16. Substrate 12 also includes a cavity 18 disposed in the first major surface 14. The cavity 18 includes a recessed surface 19. The package 10 also includes a cover layer 40 disposed over the cavity 18 and attached to the first major surface 14 of the substrate 12 to form a sealed enclosure 42. The package 10 can also include a feedthrough 20 that includes a via 22 between the recessed surface 19 of the cavity 18 and the second major surface 16 of the substrate. The feedthrough 20 can also include conductive material 24 disposed in the via 22, and an external contact 26 disposed over the via on the second major surface 16 of the substrate 12. The external contact 26 can be electrically connected to the conductive material 24 disposed in the via 22. In one or more embodiments, the external contact 26 can be sealed to the second major surface 16 of the substrate 12 using any suitable technique or combination of techniques. In one or more embodiments, the external contact 26 can be hermetically sealed to the second major surface 16 of the substrate 12. Although depicted as including five feedthroughs 20, the package 10 can include any suitable number of feedthroughs, e.g., 1, 2, 3, 4, 5, 10, 20, or more feedthroughs. Each feedthrough 20 can be substantially identical in construction. In one or more embodiments, one or more feedthroughs 20 can have characteristics that are different from one or more additional feedthroughs. The feedthrough 20 can provide an electrical pathway between the second major surface 16 and the enclosure 42 of the package 10.

In one or more embodiments, the package 10 can also include an electronic device 30 disposed within the enclosure 42. Electronic device 30 can include one or more device contacts 32 that are electrically connected to the conductive material 24 in the via 22 such that the electronic device is electrically connected to the external contact 26.

The substrate 12 can include any suitable material or combination of materials. In one or more embodiments, the substrate 12 can be a non-conductive or insulative substrate such that external electrode 26 and any conductors or other devices disposed on the substrate can be electrically isolated if desired. In one or more embodiments, the substrate 12 can include at least one of glass, quartz, silica, sapphire, silicon carbide, diamond, synthetic diamond, and gallium nitride, or alloys or combinations (including clad structures, laminates, etc.) thereof.

Further, in one or more embodiments, the substrate 12 can be substantially transparent at a desired wavelength or range of wavelengths. As used herein, the phrase "substantially transparent" as it pertains to the substrate 12 means that the substrate meets at least one or both of the following minimal energy absorption criteria: (1) the energy transmitted through the substantially transparent substrate material is sufficient to activate the bonding process at the interface via absorption by the opaque material (e.g., interface of substrate 12 and external contact 26), and (2) any energy absorbed by the transparent material will not be sufficient to melt, distort, or otherwise affect the bulk of the transparent material that is away from the bonding region. In other words, the laser bonding techniques described herein will preferentially heat only the second major surface 16 (or an outer layer at the surface 16 of the substrate 12) over the inner bulk of the substrate 12 to create an enhanced bond, such as bond 48. Such a bond may exhibit a relatively greater strength than the bulk strength of the substrate 12. Any suitable wavelength of light can be utilized provided that the substrate 12 will transmit a given percentage of the light that is directed at the substrate 12 to preferentially heat only the outer surface or outer layer instead of the inner bulk to create the enhanced bond. In one or more embodiments, the light is directed at substrate 12 though the first major surface 14 or recessed surface 19 towards the second major surface 16 (or the outer layer at the second major surface). In accordance with the foregoing, a substrate that is substantially transparent in one exemplary embodiment will transmit at least 40% of light that is directed at the substrate for a selected wavelength or range of wavelengths, assuming no reflection at the air-substrate boundaries. In accordance with the forgoing, it may be desirable to select a substrate that is substantially transmissive to light having a wavelength in a range of 10 nm to 30 μm in one or more exemplary embodiments. In one or more embodiments, a substrate that is substantially transparent may be selected that is transmissive to light of any desired wavelength. Therefore, a substantially transparent substrate 12 will allow a sufficient amount of light having a predetermined magnitude to be transmitted through the inner bulk of the substrate to the second major surface 16 to create the bond 48. In one or more embodiments, the substrate 12 can be substantially transmissive to at least one of UV light, visible light, and IR light. The light can be provided by a laser that has any suitable wavelength or range of wavelengths and any suitable pulse width.

The substrate 12 can include any suitable shape or combination of shapes and any suitable dimensions, e.g., thicknesses. Further, the substrate 12 can be a single unitary substrate or multiple substrates joined together.

The cavity 18 disposed in the first major surface 14 of the substrate 12 can take any suitable shape or combination of shapes and have any suitable dimensions. Further, the cavity 18 can be formed in the first major surface 14 of the substrate 12 using any suitable technique or combination of techniques, e.g., etching, ablation, laser-assisted etching, and combinations thereof. The recessed surface 19 of the cavity 18 can take any suitable shape or combination of shapes. In one or more embodiments, the cavity 18 can be provided by disposing a frame between a substrate that does not include a cavity formed therein and the cover layer 40.

The cover layer 40 can include any suitable material or combination of materials. In one or more embodiments, the cover layer 40 can include one or more conductive materials, e.g., copper, silver, aluminum, chromium, nickel, gold, composites (e.g., silver-filled epoxies), and alloys or combinations (including clad structures, laminates, etc.) thereof. In one or more embodiments, the cover layer 40 can include a metal foil, e.g., a titanium foil. The metal foil can have any suitable thickness. In one or more embodiments, the cover layer 40 can include one or more non-conductive materials, e.g., glass, quartz, silica, sapphire, silicon carbide, diamond, and gallium nitride, and combinations thereof.

The cover layer 40 can take any suitable shape or combination of shapes. As illustrated in FIG. 1, the cover layer 40 is substantially planar. In one or more embodiments, the cover layer 40 can include a recess that is at least partially aligned with the cavity 18 of the substrate 12 to form the enclosure 42 of the package 10.

The cover layer 40 can be attached to the substrate 12 using any suitable technique or combination of techniques. For example, an inner surface 44 of the cover layer 40 can be sealed to the first major surface 14 of the substrate 12 by the bond 48 (FIG. 2) that at least partially surrounds the cavity 18. In one or more embodiments, the bond 48 completely surrounds the cavity 18. Any suitable technique or combination techniques can be utilized to form this bond 48, e.g., the same techniques described herein for attaching the external contact 26. For example, the bond 48 can be formed using a laser to provide a laser bond. By surrounding the cavity 18 with the bond 48 that seals the cover layer 14 to the first major surface 14 of the substrate 12, the electronic device 30 and any other components disposed within the enclosure 42 can be protected from the external environment. In one or more embodiments, this bond 48 can hermetically seal the cover layer 40 to the first major surface 14 of the substrate 12. The bond 48 formed between the cover layer 40 and the first major surface 14 of the substrate 12 can take any suitable shape or combination of shapes. Further, this bond 48 can be a continuous bond or include multiple bonds, e.g., point bonds. In one or more embodiments, the bond 48 can be a bond line that forms a closed shape surrounding the cavity 18. As used herein, the term "closed shape" means that the shape is entirely enclosed such that its perimeter is unbroken and continuous.

In one or more embodiments, the bond 48 can be a bond region that surrounds the cavity 18. The bonded region can take any suitable shape or combination of shapes. In one or more embodiments, the bond 48 can include two or more shapes with one shape circumscribing the second shape. For example, the bond 48 can include two or more concentric elliptical bond lines or rings. In such embodiments, the two or more shapes may be isolated so that the shapes do not intersect or overlap. In one or more embodiments, the two or more shapes may intersect or overlap along any suitable portion or portions of the shapes. In one or more embodiments, the bond 48 can include two or more bond lines that together surround the cavity 18. For example, the bond 48 can include a series of parallel lines that are intersected by two or more lines that are non-parallel to the series of parallel lines.

In one or more embodiments, the bond 48 can include an interfacial layer between the inner surface 44 of the cover layer 40 and the first major surface 14 of substrate 12. This interfacial layer can have any suitable thickness in a direction normal to the first major surface 14 of the substrate 12. In one or more embodiments, the interfacial layer has a thickness in a direction normal to the first major surface 14 of the substrate 12 of no greater than 50 nm, 100 nm, 150 nm, 200 nm, no greater than 1000 nm, etc.

As mentioned herein, the package 10 can include one or more feedthroughs 20 to provide an electrical pathway between the second major surface 16 of the substrate 12 and the enclosure 42. Although not shown, in one or more embodiments, one or more feedthroughs 20 can also be disposed in the cover layer 40 to provide an electrical pathway between an outer surface 46 of the cover layer and the enclosure 42. Further, in one or more embodiments, one or more feedthroughs 20 can also be formed between the enclosure 42 and an end surface 13 of the substrate 12 (also not shown).

The feedthrough 20 can include the via 22 between the second major surface 16 of the substrate 12 and the recessed surface 19 of the cavity 18. The via 22 can be any suitable size and take any suitable shape. The size and shape of the via 22 can be predicated on the thickness of the substrate 12 and the techniques utilized to provide the conductive material that forms the electrical pathway between the second major surface 16 and the recessed surface 19 of the substrate 12. Exemplary shapes for the via 22 may include parallel surface walls and tapered surface walls. In one or more exemplary embodiments where the substrate 12 has a thickness of approximately 100 to 500 µm, the via 22 can have an opening at the second major surface 16 of the substrate that is no greater than 500 µm, that is no greater than 250 µm, no greater than 100 µm, no greater than 80 µm, no greater than 50 µm, or no greater than 10 µm. In one or more example embodiments where the substrate 12 has a thickness of approximately 100 to 500 µm, the via 22 can also have an opening at the recessed surface 19 of the substrate 12 that has a diameter of no greater than 500 µm, no greater than 250 µm, no greater than 100 µm, no greater than 80 µm, no greater than 50 µm, or no greater than 10 µm. Of course, the diameter of the via 22 could be larger (or smaller) than the illustrated examples based on the substrate thickness and/or the techniques utilized to provide the conductive material that forms the electrical pathway. Any suitable technique or combination of techniques can be utilized to form the via 22, e.g., drilling, chemical etching, laser etching, etc.

The feedthrough 20 can also include conductive material 24 disposed in the via 22 to provide a conductive pathway between the second major surface 16 and the recessed surface 19 of substrate 12. The conductive material 24 can include any suitable conductive material or combination of conductive materials, e.g., copper, titanium, aluminum, chromium, nickel, gold, composites (e.g., silver-filled epoxies), and combinations thereof. The conductive material 24 can be disposed in the via 22 using any suitable technique or combination of techniques to provide a conductive pathway between the external contact 26 to one or more devices or contacts disposed within the sealed enclosure 42. In one or more embodiments, the conductive material 24 can be disposed in the via 22 such that it substantially fills the via. In one or more embodiments, the conductive material 24 can be disposed in the via 22 along sidewalls of the via and the opening of the via at the second major surface 16.

As mentioned herein, the feedthrough 20 includes the external contact 26. In one or more embodiments, the external contact 26 can be adapted to electrically connect the feedthrough 20 to a conductor or a contact of a device, e.g., the device contact 32 of the electronic device 30. Such conductors and contacts can be electrically connected to the external contact 26 using any suitable technique or combination of techniques, e.g., soldering, physical contact, welding, etc. The external contact 26 can include any suitable conductive material or combination of conductive materials, e.g., copper, silver, titanium, niobium, zirconium, tantalum, stainless steel, platinum, iridium, or alloys or combinations (including clad structures, laminates, etc.) thereof. In one or more embodiments, the external contact 26 can include two or more materials, e.g., bi-metals, clad structures, or laminates, etc.

The external contact 26 can take any suitable shape or combination of shapes. In one or more embodiments, the external contact 26 can take a circular shape in a plane parallel to the second major surface 16 of the substrate 12. In one or more embodiments, the external contact 26 can take a rectangular shape in the plane parallel to the second major surface 16 of the substrate 12. Further, the external contact 26 can take any suitable shape or combination of shapes in a plane orthogonal to the second major surface 16 of the substrate 12, e.g., square, tapered, domed, etc. In one or more embodiments, the contact 26 can take substantially the same shape as an external contact of one or more additional feedthroughs 20. In one or more embodiments, external contact 26 can take a shape that is different from the shape of an external contact of one or more additional feedthroughs 20. Further, in one or more embodiments, one or more external contacts 26 can include complex shapes such as grooves or channels formed in the contact to facilitate attachment of conductors or electronic devices to the contacts.

The external contact 26 can also include any suitable dimensions. In one or more embodiments, the contact 26 can have any suitable thickness in a direction normal to the second major surface 16 of the substrate 12. It is envisioned that for purposes of this disclosure, the dimension of the contact thickness is limited only by the fabrication techniques utilized to form the contact 26. In one or more exemplary embodiments, this thickness can be at least 5 μm. In one or more embodiments, the thickness can be no greater than 10 mm, although greater thicknesses are also contemplated. The thickness of the contact 26 can be the same as or different from the thickness of an external contact of one or more additional feedthroughs 20. In one or more embodiments, the external contact 26 can be of sufficient size and thickness to enable laser, resistance, or other welding and joining techniques to be utilized to electrically couple conductors and/or electronic devices to the external contact.

In one or more embodiments, the external contact 26 can be formed or disposed over the via 22 on the second major surface 16 of the substrate 12. For purposes of the present disclosure, the terms "form," "forming," and "formed" will be used interchangeably with the terms "dispose," "disposing," and "disposed" respectively, such that the terms are considered to be equivalent. In other words, the external contact 26 is disposed over the via 22 such that the contact covers the via and the via is not visible in a plan view of the second major surface 16 of the substrate 12. In one or more embodiments, the external contact 26 (or any of the external contacts described herein) can be formed separate from the substrate 12 as a discrete member, or it could be patterned from a conductive sheet or foil as described herein (e.g., in reference to FIGS. 8A-I), and disposed over the via 22 by attaching the formed contact to the second major surface 16 of the substrate 12.

The external contact 26 is electrically connected to the conductive material 24 that is disposed in the via 22. In one or more embodiments, the external contact 26 is in direct contact with the conductive material 24 to electrically connect the contact to the conductive material. In one or more embodiments, one or more additional conductive layers can be disposed between the external contact 26 and the conductive material 24 to electrically couple the external contact to the conductive material.

In one or more embodiments, the external contact 26 is hermetically sealed to the second major surface 16 of the substrate 12. Any suitable technique or combination of techniques can be utilized to hermetically seal the external contact 26 to the second major surface 16 of the substrate 12. For example, in one or more embodiments, the external contact 26 can be hermetically sealed to the second major surface 16 of the substrate 12 by a bond 50 (FIG. 3) that surrounds the via 22. Any suitable technique or combination of techniques can be utilized to form this bond 50. For example, in one or more embodiments, the bond 50 can be formed using a laser to provide a laser bond. By surrounding the via 22 with the bond 50 that hermetically seals the external contact 26 to the second major surface 16 of the substrate 12, the via is also protected from the external environment. The electrical connection between the external contact 26 and the conductive material 24 disposed in the via 22 is, therefore, protected, and the integrity of this electrical pathway from the second major surface 16 of the substrate 12 to the recessed surface 19 of the cavity 18 can be maintained. In one or more embodiments, the external contact 26 can also be attached to the second major surface 16 of the substrate 12 using bonds in addition to bond 50. For example, in one or more embodiments, the external contact 26 can be attached to the second major surface 16 by bond 50 and one or more additional bonds between the external contact 26 and the second major surface, e.g., point bonds.

Figure 3:
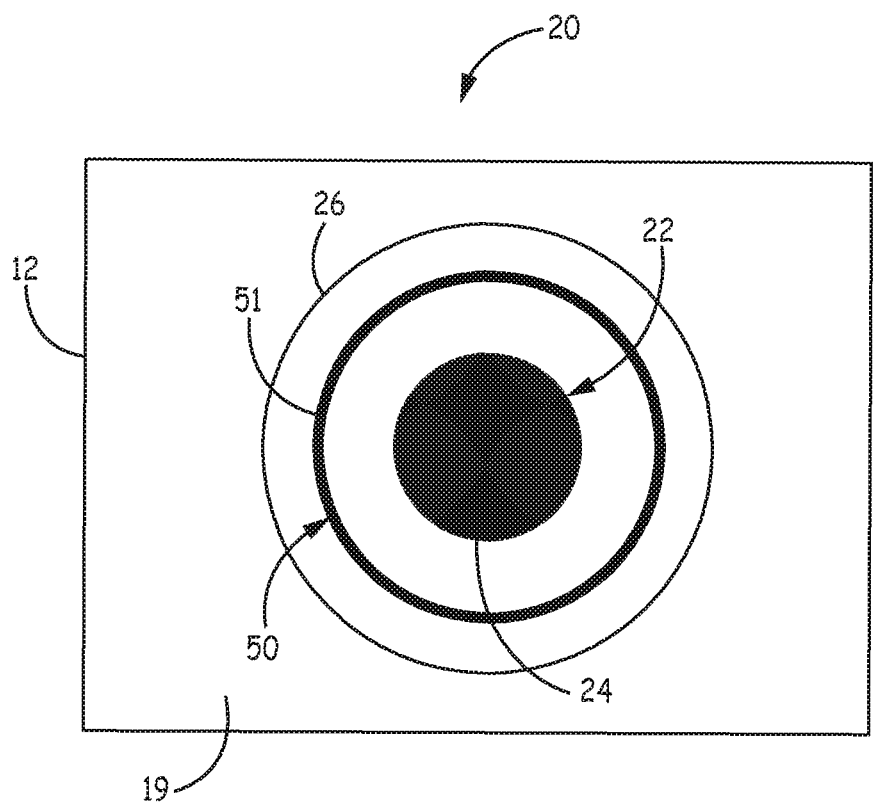
FIG. 3 is a schematic plan view of a feedthrough of the sealed package of FIG. 1.

FIG. 3 is a schematic plan view of a portion of the package 10 that includes feedthrough 20 of the assembly 10 of FIG. 1. The feedthrough 20 is shown as viewed through the recessed surface 19 of the cavity 18. The feedthrough 20 includes the external contact 26, the via 22 including the conductive material 24 disposed in the via, and the bond 50. The bond 50 hermetically seals the external contact 26 to the second major surface 16 of the substrate 12. The bond 50 can take any suitable shape or combination of shapes such that it surrounds the via 22 as shown in FIG. 3. In one or more embodiments, the bond 50 can be a bond line 51. In one or more embodiments, the bond line 51 can form a closed shape in a plane parallel to the second major surface 16 of the substrate 12. Any suitable closed shape or shapes can be formed by bond line 51, e.g., elliptical, rectilinear, triangular, polygonal, etc.

In one or more embodiments, the bond 50 can be a bonded region that surrounds the via 22. The bonded region can take any suitable shape or combination of shapes. In one or more embodiments, the bond 50 can include two or more shapes with one shape circumscribing the second shape. For example, the bond 50 can include two or more concentric elliptical bond lines or rings. In such embodiments, the two or more shapes may be isolated so that the shapes do not intersect or overlap. In one or more embodiments, the two or more shapes may intersect or overlap along any suitable portion or portions of the shapes. In one or more embodiments, the bond 50 can include two or more bond lines that together surround the via 22. For example, the bond 50 can include a series of parallel lines that are intersected by two or more lines that are non-parallel to the series of parallel lines.

In one or more embodiments, the bond 50 can include an interfacial layer between the external contact 26 and the second major surface 16 of the substrate 12. It should be understood that the thickness of the interfacial layer is in part dependent on the intended function. For example, it may be desirable to form the interfacial layer as a stress buffer, a barrier, or a spacer. Therefore, this interfacial layer can have any suitable thickness in a direction normal to the second major surface 16. In one or more embodiments, the interfacial layer has a thickness in a direction normal to the second major surface 16 of no greater than 10 nm, 100 nm, 150 nm, 200 nm, 500 nm, or 10 μm.

Figure 2:
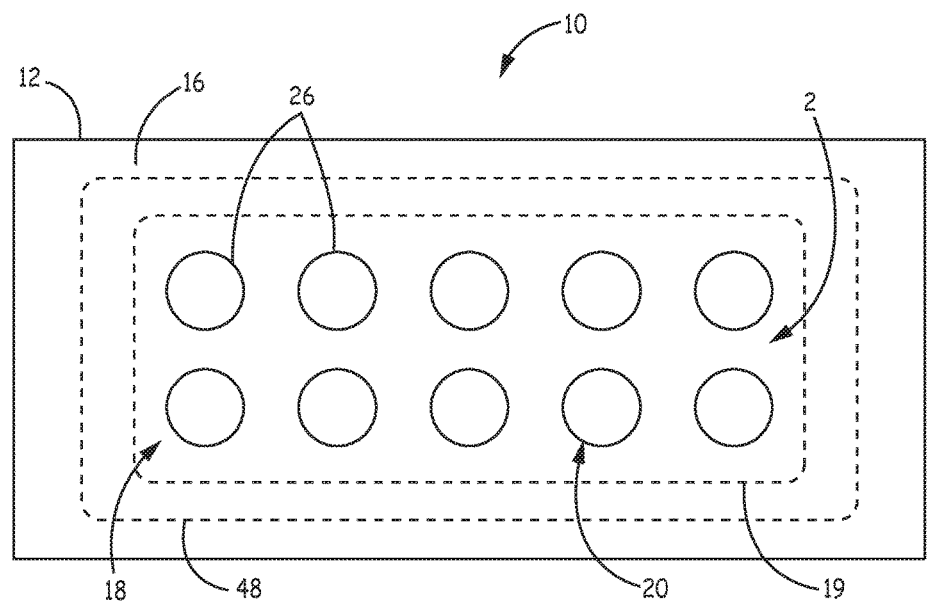
FIG. 2 is a schematic plan view of the sealed package of FIG. 1.
Figure 4:
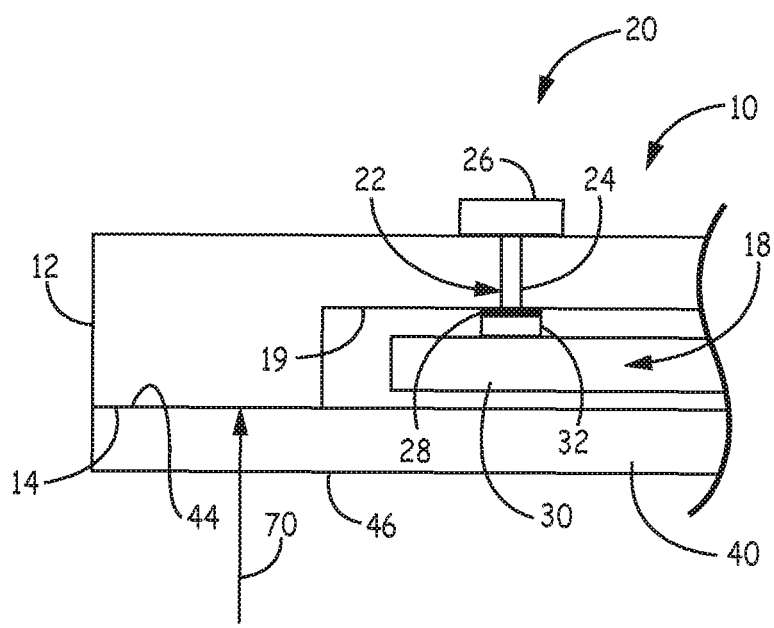
FIG. 4 is a schematic cross-section view of a portion of the sealed package of FIG. 1.

As mentioned herein, any suitable technique or combination of techniques can be utilized to form bond 48 between the inner surface 44 of the cover layer 40 and the first major surface 14 of the substrate 12, and to form bond 50 between the external contact 26 of the feedthrough 20 and the second major surface 16 of the substrate, e.g., the techniques described in co-owned U.S. Patent Application No. 62/096,706 (Medtronic Reference No. C00008775.USP1), entitled KINETICALLY LIMITED NANO-SCALE DIFFUSION BOND STRUCTURES AND METHODS. For example, FIG. 4 is a schematic cross-section view of a portion of the package 10 of FIG. 1. In one or more embodiments, electromagnetic radiation 70 (e.g., light such as laser light) can be directed through the outer surface 46 of the cover layer 40 and directed (and/or focused) at an interface between the inner surface 44 of the cover layer and the first major surface 14 of the substrate 12 to form bond 48 (FIG. 2). Further, electromagnetic radiation (e.g., electromagnetic radiation 70) can also be directed through the recessed surface 19 of substrate 12, and focused at a region or an interface between the second major surface 16 of the substrate and the external contact 26 to form bond 50 prior to connecting the electronic device 30 to the internal contact 28 and attaching the cover layer 40 to the first major surface 14 of the substrate 12. The properties of the electromagnetic radiation 70 can be selected based on the material of the substrate 12 and the cover layer 40, and/or thickness and materials of the external contact 26, and controlled in a predetermined to form bonds 48, 50. For example, the electromagnetic radiation 70 can include laser light having a suitable wavelength or range of wavelengths and a predetermined pulse width or range of pulse widths in one or more embodiments. The properties of the electromagnetic radiation 70 are predicated on preferentially heating the interface of the substrate 12 and the external contact 26 to create an enhanced bond, such as bond 50, having a relatively greater strength than the bulk strength of the substrate 12. Accordingly, a substrate that is substantially transparent may be selected that is transmissive to light of any desired wavelength. In one or more embodiments, the laser light 70 can include light having a wavelength in a range of 10 nm to 30 µm. In one or more embodiments, the laser light can include a wavelength of no greater than 2000 nm. For example, laser light 70 can include UV light, visible light, IR light, and combinations thereof. The UV light can be provided by a UV laser that has any suitable wavelength or range of wavelengths and any suitable pulse width. In one or more embodiments where the thickness of the substrate 12 is approximately 100 to 500 µm, a laser can be utilized to provide light 70 having a wavelength in a range of 10 nm to 30 µm and a pulse width in a range of 1 ns to 100 ns. In one or more embodiments, the materials for the substrate 12, cover layer 40, and the external contact 26, and the power level, pulse width, and wavelength of the light used may be selected such that the light may not directly damage, ablate, warp, or cut the substrate, cover layer, and the contact, and such that the substrate, cover layer, and the contact retain their bulk properties.

In general, light 70 can be provided by any suitable laser or laser system. For example, the laser may generate light having a relatively narrow set of wavelengths (e.g., a single wavelength). In one or more embodiments, the light 70 emitted by the laser may form a collimated beam that may not be focused at a particular point. In one or more embodiments, the light 70 emitted by the laser may be directed (and/or focused) at a focal point at an interface between the inner surface 44 of the cover layer 40 and the first major surface 14 of the substrate 12 to generate a laser bond 48. Further, in one or more embodiments, the light emitted by the laser may be focused at a focal point at a region or an interface between the external contact 26 and the second major surface 16 of the substrate 12 to generate the laser bond 50.

Although the laser may provide light 70 that has a narrow range of wavelengths, in one or more embodiments, the laser may represent one or more devices that emit electromagnetic radiation having a wider range of wavelengths than a single typical laser. A wide variety of devices may be used to emit electromagnetic radiation having a narrow or wide range of wavelengths. In one or more embodiments, the laser may include one or more laser devices including diode and fiber lasers. Laser sources may also include, e.g., carbon dioxide lasers, TI sapphire lasers, argon ion lasers, Nd:YAG lasers, XeF lasers, HeNe lasers, Dye lasers, GaAs/AlGaAs lasers, Alexandrite lasers, InGaAs lasers, InGaAsP lasers, Nd:glass lasers, Yb:YAG lasers, and Yb fiber lasers. The laser device may also include one of continuous wave, modulated, or pulsed modes. Accordingly, a wide variety of laser devices may be used in the bonding process. In one or more embodiments, laser fluence of 1-2 $J/cm^2$ may be used, with a top hat, Gaussian, or other suitable spatial energy profile.

In one or more embodiments, the feedthrough 20 can include an internal contact 28 disposed on the recessed surface 19 of the recess 18. The internal contact 28 can include any suitable material or combination materials, e.g., the same materials utilized for the external contact 26. Further, the internal contact 28 can take any suitable shape or combination of shapes and have any suitable thickness in a direction normal to the recessed surface 19, e.g., the same shapes and thicknesses as described regarding the external contact 26.

Figure 5:
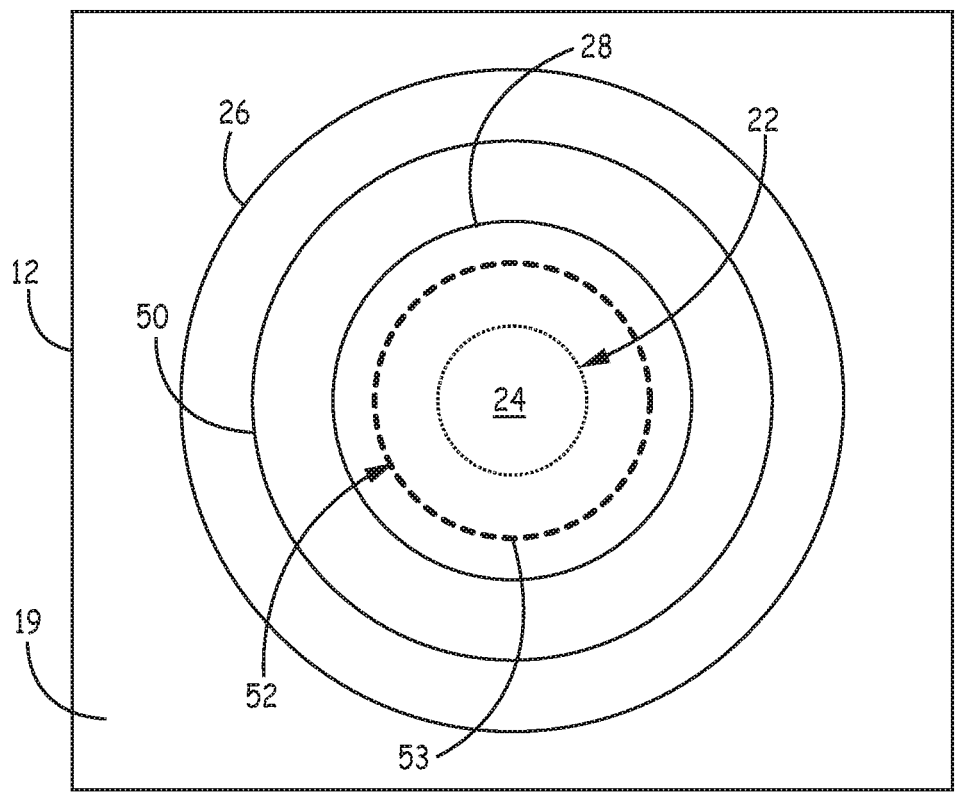
FIG. 5 is a schematic plan view of a feedthrough of the sealed package of FIG. 1.

The internal contact 28 is disposed over the via 22 on the recessed surface 19. The contact 28 can be electrically connected to the conductive material 24 disposed in the via 22. In one or more embodiments, the internal contact 28 is hermetically sealed to the recessed surface 19 using any suitable technique or combination of techniques, e.g., by a bond (e.g., laser bond) that surrounds the via 22. For example, FIG. 5 is a schematic plan view of a portion of the package 10 of FIG. 1. In FIG. 5, the internal contact 28 is shown as viewed from the recessed surface 19 of the substrate 12. As shown in FIG. 5, the internal contact 28 is attached to the recessed surface 19 by bond 52, which is shown in dashed lines to indicate that the bond is not visible in this view of package 10. Also shown in FIG. 5 is external contact 26 hermetically sealed to the outer surface of substrate 12 by bond 50.

In one or more embodiments, the internal contact 28 can be smaller than the external contact 26 in a dimension in the plane parallel to the second major surface 16 of the substrate 12. In one or more embodiments, the internal contact 28 can be the same dimension or dimensions as external contact 26. In one or more embodiments, the internal contact 28 can be larger than the external contact 26 in a dimension in the plane parallel to the second major surface 16 of the substrate 12. Further, the internal contact 28 can take the same shape or combination of shapes as the external contact 26. In one or more embodiments, the internal contact 28 can take a shape that is different from the shape of the external contact 26.

In one or more embodiments, the external contact 26 can be larger than the internal contact 28 such that the internal contact can first be attached to the recessed surface 19, e.g., by directing light through the substrate 12 from the second major surface 16 to a region or interface between the internal contact and the recessed surface 19 to form bond 52. The external contact 26 can, in one or more embodiments, be hermetically sealed to the second major surface 16 of the substrate 12 by directing light through the recessed surface to the region or interface between the external contact and the second major surface to form bond 50 without the internal contact 28 being between the light and the region where the bond 50 is formed. In one or more embodiments, the external contact 26 and the internal contact 28 can be relatively the same size. In such embodiments, the external contact 26 and/or the internal contact 28 can be attached to the substrate 12 in any suitable order. For example, the external contract 26 can be attached to the second major surface 16 using light to form bond 50. The internal contact 28 can then be attached to the recessed surface 19 by directing light at an angle into the substrate 12 from the second major surface 16 such that the external contact 26 does not block the light as it forms bond 52 to attach the internal contact 28 to the recessed surface 19. In one or more embodiments, one or both of the external contact 26 and the internal contact 28 can be bonded to the second major surface 16 and the recessed surface 19, respectively, to form a hermetic seal. In one or more embodiments, only one of the bonds 48, 50 is formed as a hermetic seal.

As with bond 50, bond 52 can, in one or more embodiments, take any suitable shape or combination of shapes and have any suitable dimensions, e.g., the shapes and dimensions described for bond 50. For example, as illustrated in FIG. 5, bond 52 can include a bond line 53. In one or more embodiments, bond 52 can include any suitable size and shaped region or regions that surround the via 22. Further, as is also the case with bond 50, bond 52 can include an interfacial layer between the recessed surface 19 and the internal contact 28. This interfacial layer can have any suitable thickness, e.g., the same thicknesses as those described for bond 50. In one or more embodiments, the bond 52 can be a laser bond.

As mentioned herein, any suitable conductors or contacts can be formed on one or both of the recessed surface 19 and the second major surface 16 of the substrate 12. For example, as shown in FIG. 1, one or more conductors 60 can be formed on the second major surface 16 of the substrate 12. Further, one or more conductors 62 can be disposed on the recessed surface 19. Any suitable number of conductors can be formed on one or both of the second major surface 16 and the recessed surface 19. Any suitable technique or combination of techniques can be utilized to form conductors 60, 62, e.g., chemical vapor deposition, plasma vapor deposition, physical vapor deposition, plating, etc., followed by photolithography, chemical etching, etc. In one or more embodiments, a conductive material layer can be formed on one or both of the outer surface 16 and recessed surface 19, and the conductive material layer can be patterned to form conductors 60, 62. Further, the conductors 60, 62 can include any suitable conductive material or combination of conductive materials. In one or more embodiments, the conductor 60 can electrically connect two or more external contacts 26 together, and conductor 62 can electrically connect two or more internal contacts 28 together. In one or more embodiments, any of conductors 60, 62 can be connected to one or more suitable electronic device(s). In one or more embodiments, one or both of conductors 60, 62 can be formed to provide an antenna for communication with one or more electronic devices electrically coupled to the package 10. Further, in one or more embodiments, one or both of conductors 60, 62 can form an inductive coil that can be utilized to provide inductive coupling to an external inductive power supply. For example, if the package 10 is included in an implantable medical device, then conductor 60 can be used to form an inductive coil that can receive inductive energy from an external inductive power supply to provide power to the implantable medical device. In one or more embodiments, the inductive coil can be formed by patterning one or more of the external contacts 26.

Figure 7:
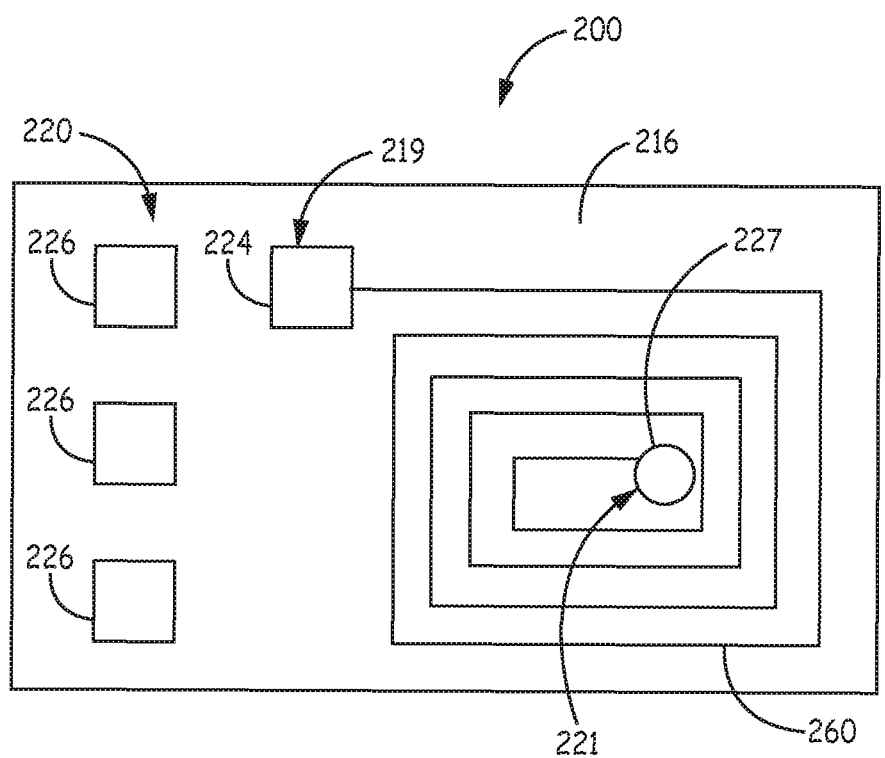
FIG. 7 is a schematic plan view of another embodiment of a sealed package.

For example, FIG. 7 is a schematic plan view of another embodiment of a sealed package 200. All of the design considerations and possibilities regarding the sealed package 10 of FIGS. 1-5 apply equally to the sealed package 200 of FIG. 7. Package 200 includes feedthroughs 220. Each feedthrough 220 includes an external contact 226 that can be electrically connected to an internal contact, conductor, or device. The assembly 200 also includes a conductor 260 that is electrically connected to external contact 227 of feedthrough 221 and external contact 224 of feedthrough 219. In one or more embodiments, the conductor 260 is adapted to form an antenna that can provide wireless communication to one or more electronic devices disposed within the package 200, e.g., electronic device 30 of package 10 of FIG. 1. In one or more embodiments, the conductor 260 can be adapted to form an inductive coil that can be inductively coupled with a power source to provide power to one or more devices electrically coupled to feedthroughs 219 and 221.

Returning to FIGS. 1-5, the conductors 60, 62 can take any suitable shape or combination of shapes and have any suitable dimensions. Further, one or more conductors 60, 62 can electrically connect the package 10 to ground, e.g., on an enclosure or housing of an implantable medical device that includes the package.

Each of the conductors 60, 62 can be formed in separate steps. In one or more embodiments, conductors on either or both of the second major surface 16 and the recessed surface 19 can be formed simultaneously with the conductive material 24 disposed in the via and/or the external or internal contacts 26, 28.

In one or more embodiments, one or more conductors 60, 62 can be disposed such that the conductors are electrically connected to a contact, and the conductive material 24 disposed in the via 22. In such embodiments, one or both of the bond 50 and the bond 52 would be formed between the contact, the conductor, and the substrate 12 such that electrical connection between the contact, the conductor, and the conductive material is maintained.

As mentioned herein, sealed package 10 can include one or more electronic devices 30 disposed within the enclosure 42. The electronic device 30 includes one or more device contacts 32 that can be electrically connected to one or more feedthroughs 20. For example, device contact 32 can be electrically connected to the conductive material 24 disposed within the via 22 such that the electronic device 30 is electrically connected to the external contact 26. The device contact 32 can be directly connected to the conductive material 24 in the via 22. In one or more embodiments, one or more conductive layers can be disposed between the device contact 32 and the conductive material 24 disposed within the via 22. For example, the device contact 32 can be electrically connected to conductor 62, which can be electrically connected to the conductive material 24 and via 22, thereby providing an electrical pathway between the device 32 and the external contact 26. In one or more embodiments, the device contact 32 can be electrically connected to the internal contact 28.

The electronic device 30 can be disposed in any suitable location within the enclosure 42. In one or more embodiments, the electronic device 30 is disposed within the enclosure 42 such that the device is attached to the recessed surface 19 of the cavity 18. In one or more embodiments, the electronic device 30 can be attached to the cover layer 40 and electrically connected to one or more feedthroughs 20 when the cover layer is attached to the substrate 12.

Any suitable electronic device 30 or devices can be disposed within the enclosure 42, e.g., one or more power sources, capacitors, transistors, integrated circuits, including controllers and multiplexers, and combinations thereof. Any suitable number of electronic devices 30 can be disposed within the enclosure 42. In one or more embodiments, the electronic device 30 can be formed on the recessed surface 19 or on the cover layer 40. In one or more embodiments, the electronic device 30 can be formed separately and then attached to the recessed surface 19, attached to the cover layer 40, or attached to both the recessed surface and the cover layer. Any suitable technique or combination of techniques can be utilized to attach the electronic device 30 to one or both of the recessed surface 19 in the cover layer 40, e.g., a bond (e.g., bond 50 of FIG. 4) can be formed between the electronic device and the recessed surface 19.

The electronic device 30 can be electrically connected to one or more additional electronic devices disposed within the enclosure 42. In one or more embodiments, the electronic device 30 can be electrically connected to the conductive material 24 disposed in one or more vias 22. Any suitable technique or combination of techniques can be utilized to electrically connect the electronic device 30 to the conductive material 24, e.g., one or more conductors 62 can be disposed on the recessed surface 19, or the electronic device can be attached to one or more internal contacts 28. Further, in one or more embodiments, the electronic device 30 can be electrically connected to other electronic circuitry or devices disposed adjacent the substrate 12.

As mentioned herein, the various embodiments of sealed packages described herein can include any suitable number of feedthroughs. The feedthroughs can be disposed in any suitable arrangement. In one or more embodiments, the feedthroughs can be disposed in a random configuration. In one or more embodiments, the feedthroughs can be disposed in an array. For example, as illustrated in FIG. 2, the sealed package 20 includes feedthroughs 20 disposed in the substrate 12. The feedthroughs 20 can be disposed in an array 2. The array 2 can include any suitable number of feedthroughs 20. And the feedthrough array 2 can include any suitable arrangement of feedthroughs 20.

Figure 6:
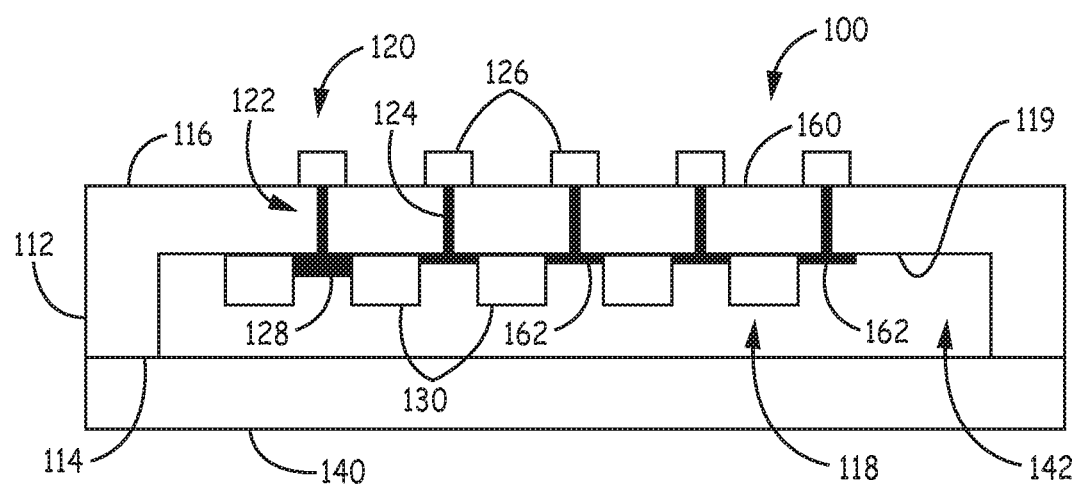
FIG. 6 is a schematic cross-section view of another embodiment of a sealed package.

The sealed packages described herein can include any suitable additional elements or devices. For example, FIG. 6 is a schematic cross-section view of another embodiment of a sealed package 100. All of design considerations and possibilities regarding the package 10 of FIGS. 1-5 apply equally to the package 100 of FIG. 6. The package 100 includes a substrate 112 having a first major surface 114 and a second major surface 116, and a cavity 118 formed or disposed in the first major surface 114, where the cavity includes a recessed surface 119. The package 100 also includes one or more feedthroughs 120. A cover layer 140 can be disposed over the cavity 118 and attached to the first major surface 114 of the substrate 112 to form a sealed enclosure 142.

One difference between package 100 and package 10 is that several electronic devices 130 are disposed on or connected to the recessed surface 119 of cavity 118. Any suitable electronic device can be disposed on the recessed surface 119, e.g., capacitors, transistors, integrated circuits, including controllers and multiplexers, etc. Further, any suitable number of electronic devices 130 can be disposed on the recessed surface 119. Any suitable technique or combination of techniques can be utilized to dispose the electronic devices 130 on the recessed surface 119. In one or more embodiments, the electronic devices 130 can be formed on the recessed surface 119 of the substrate 112. In one or more embodiments, each of the devices 130 can be formed separately and then attached to the recessed surface 119. Any suitable technique or combination of techniques can be utilized to attach the electronic devices 130 to the recessed surface 119, e.g., a bond (e.g., bond 50 of FIG. 3) can be formed between the electronic device and the recessed surface.

Each of the electronic devices 130 can be electrically connected to one or more additional electronic devices disposed on the recessed surface 119 or within the enclosure 142. In one or more embodiments, the electronic devices 130 can be electrically connected to conductive material 124 disposed in one or more vias 122. Any suitable technique or combination of techniques can be utilized to electrically connect the electronic devices 130 to the conductive material 124, e.g., one or more conductors 162 can be disposed on the recessed surface 119, or one or more the electronic devices 130 can be attached to an internal contact 128. Further, in one or more embodiments, the electronic devices 130 can be electrically connected to other electronic circuitry or devices disposed adjacent the substrate 112. In one or more embodiments, the feedthrough 120 can provide a conductive pathway between the second major surface 116 and one or more electronic devices 130.

Returning to FIGS. 1-5, the external contacts 26 can be disposed in any suitable arrangement. In one or more embodiments, the external contacts 26 can be disposed in a two-dimensional arrangement such as an array (e.g., array 2 of FIG. 2), or a three-dimensional arrangement. In other words, the sealed package 10 can include a substrate having a three-dimensional shape, e.g., spherical, cubic, conical, etc. In such embodiments, one or more feedthroughs 20 can be disposed in any arrangement such that the external contacts 26 can be provided in a three-dimensional configuration. See, e.g., co-owned U.S. Pat. No. 7,822,482 to Gerber.

The various embodiments of sealed packages described herein (e.g., sealed package 10 of FIGS. 1-5) can be formed using any suitable technique or combination of techniques. In general, the sealed packages described herein can be formed as single, discrete packages. In one or more embodiments, two or more sealed packages can be formed on a substrate or wafer and then singulated using any suitable technique or combination of techniques.

FIGS. 8A-I are schematic views of one embodiment of a method 300 of forming a sealed package 310. All of the design considerations and possibilities regarding the sealed package 10 of FIGS. 1-5 apply equally to sealed package 310 of FIGS. 8A-I. In FIG. 8A, a substrate 312 is provided. A first major surface 314 and a second major surface 316 of the substrate 312 can be prepared by polishing to remove surface deformities such as burrs, gouges, ridges, or other irregularities. Different techniques may be used to polish first major surface 314 and second major surface 316. For example, surfaces 314, 316 can be mechanically polished, chemically polished, or treated by chemical-mechanical polishing (CMP) techniques. Surfaces 314, 316 can be polished until the surfaces exhibit comparatively low surface roughness values that enhance direct bond formation. Although surfaces 314, 316 may be polished to remove irregularities, the bonding process according to the present disclosure may not require the surfaces to be as smooth as surfaces used during typical wafer bonding techniques. Surfaces 314, 316 may be cleaned to remove particles and contaminates. Cleaning surfaces 314, 316 can include ultrasonic and/or megasonic cleaning.

In FIG. 8B, a cavity 318 can be formed in the first major surface 314 of the substrate 312. Any suitable technique or combination of techniques can be utilized to form the cavity 318, e.g., etching, ablation, laser-assisted etching, and combinations thereof. The cavity 318 includes a recessed surface 319. The recessed surface 319 can be polished using any suitable technique or combination of techniques, e.g., the techniques described herein utilized to polish the first and second major surfaces 314, 316 of the substrate 312.

One or more vias 322 can be disposed in or formed between the first major surface 314 and the second major surface 316 of the substrate 312 as shown in FIG. 8C. Although illustrated as including two vias, the sealed package 310 can include any suitable number of vias. Further, any suitable technique or combination of techniques can be utilized to form via 322, e.g., drilling, etching, laser drilling, etc.

Although not shown, one or more conductors (e.g., conductor 60 of FIG. 1) can optionally be formed on at least one of the first major surface 314 and the second major surface 316. Any suitable technique or combination of techniques can be utilized to form such conductors. For example, in one or more embodiments, a conductive material layer (not shown) can be formed on the second major surface 316. The conductive material layer can be formed, e.g., using plasma vapor deposition, chemical vapor deposition, physical vapor deposition, etc. One or more portions of the conductive material layer can then be removed to form the conductors using any suitable technique or combination of techniques, e.g., photolithography, etc. Any suitable number of conductors can be formed on the second major surface 316 of substrate 312.

One or more external contacts 326 can be formed on the second major surface 316 of substrate 312 using any suitable technique or combination of techniques. For example, as illustrated in FIG. 8D, a conductive material layer 325 can be disposed on and/or coupled to the second major surface 316 over the conductors (if present) and the vias 322. In one or more embodiments, the conductive material layer 325 can be attached to the second major surface 316 of the substrate 312 using any suitable technique or combination of techniques, e.g., forming a bond that hermetically seals the conductive layer to the second major surface. The conductive material layer 325 can be attached to the second major surface 316.

Any suitable technique or combination of techniques can be utilized to attach the conductive layer 325 to the second major surface 316, e.g., the techniques described in U.S. Patent Application No. 62/096,706 (Medtronic Reference No. C00008775.USP1), entitled KINETICALLY LIMITED NANO-SCALE DIFFUSION BOND STRUCTURES AND METHODS. For example, electromagnetic radiation can be directed through substrate 312 from the first major surface 314 to an interface between the conductive layer 325, the conductors (if present), and the second major surface 316. The electromagnetic radiation can form a bond (e.g., bond 50 of FIG. 5) that hermetically seals the conductive layer 325 to the substrate 312 in any suitable pattern or shape. The bond can be a laser bond. In one or more embodiments, a bond surrounds the via 322.

As illustrated in FIG. 8E, one or more portions of the conductive material layer 325 can be removed to form one or more external contacts 326 on the second major surface 316 of the substrate 312. Any suitable technique or combination of techniques can be utilized to form the external contacts 326, e.g., photolithography, etching, laser ablation, etc. In or more embodiments, a mask or masks can be formed on the second major surface 316 of the substrate 312, and the conductive material layer 325 can be formed over the mask. Portions of the conductive material layer 325 that are formed on the mask itself can be removed using any suitable technique or combination of techniques, including photolithography, etching, laser ablation etc., to form external contacts 326. In addition, one or more portions of the conductive material layer 325 can also be removed or patterned to create other electrical components, such as an antenna.

The bond formed between the external contact 326 and the second major surface 316 remains intact such that it hermetically seals the contact to the second major surface. In other words, portions of the conductive layer 325 that are hermetically sealed to the second major surface 316 are not removed when the external electrodes 326 are patterned. Similar techniques can be utilized to form internal contacts on the recessed surface 319 of the cavity 318. The external contact 326 can be electrically connected to the conductors (if present).

Conductive material 324 can be formed in the via 322 as shown in FIG. 8F. Any suitable technique or combination of techniques can be utilized to form or dispose the conductive material 324 in the vias 322, e.g., plasma vapor deposition, chemical vapor deposition, physical vapor deposition (e.g., sputtering), plating, conductive composite pastes, etc. Further, the conductive material 324 may substantially fill the vias 322. In one or more embodiments, conductive material 324 can be formed on one or more sidewalls of the vias 322 to form or dispose one or more conductors within the via.

In one or more embodiments, the recessed surface 319 of the recess 318 can be polished to remove any excess conductive material 324. Any suitable technique or combination techniques can be utilized to polish the recessed surface 319.

In one or more embodiments, one or more conductors that have been disposed on one or both of the recessed surface 319 and the second major surface 316 can be electrically connected to the conductive material 324 in the vias 322. In such embodiments, such conductors can be electrically connected using any suitable technique, e.g., the electrical conductors are in physical contact with the conductive material. In one or more embodiments, the conductors and the conductive material 324 can include the same material or combination of materials. Further, in one or more embodiments, the conductors and the conductive material 324 can be formed or disposed simultaneously or sequentially.

In FIG. 8G, one or more internal contacts 328 can be formed or disposed on the recessed surface 319 of the cavity 318 to provide feedthrough 520. In one or more embodiments, one or more of the internal contacts 328 can be disposed over the via 322 such that the internal contacts 328 are electrically connected to the conductive material 324 disposed in the vias. Any suitable technique or combination of techniques can be utilized to form internal contacts 328, e.g., the same techniques described herein regarding the external contacts 326. In one or more embodiments, the external contact 326, the via 322, the conductive material 324 disposed in the via, and the internal contact 328 provide a feedthrough 320 that can provide an electrical pathway between the cavity 318 and the second major surface 316 of the substrate 312. In one or more embodiments, the feedthroughs 320 can be provided by the external contact 326, the via 322 and the conductive material 324 disposed within the via and does not include an internal contact 328 as is further described herein.

One or more electronic devices 330 can be disposed at least partially within the cavity 318 as shown in FIG. 8H. Electronic device 330 can include any suitable electronic device or devices. In one or more embodiments, the electronic device 330 can include a power source that can be at least partially disposed within the cavity 318 prior to attaching a cover layer 340 to the first major surface 314 of the substrate 312. The power source can be electrically connected to one or more electronic devices disposed within the cavity 318.

The electronic device 330 can be disposed at least partially within the cavity 318 such that a device contact 332 of the electronic device is electrically connected to the conductive material 324 in the via 322. The electronic device 330 can include any suitable number of device contacts 332.

The electronic device 330 can, therefore, be electrically connected to the external contact 326 when the device contact 332 is electrically connected to the conductive material 324 disposed within the via 322. In other words, an electrical pathway can be provided between the electronic device 330 and the second major surface 316 of the substrate 312 by electrically connecting the device to the feedthrough 320. In one or more embodiments, the device contact 332 can be electrically connected directly to the conductive material number 324 without an intervening internal contact 328 being present. Optionally, an insulative material (not shown) can be disposed within the cavity 318 such that the insulative material at least partially surrounds the electronic device 330. The insulative material, therefore, can be disposed within a sealed enclosure 342 that is formed by the cover layer 340 being disposed on the first major surface 314 of the substrate 312 as is further described herein. Any suitable insulative material or combination of materials can be disposed within the cavity 318 such that the insulative material at least partially surrounds the electronic device 330.

As shown in FIG. 8I, the cover layer 340 can be disposed over the cavity 318. The cover layer 340 can be attached to the first major surface 314 of the substrate 312 to form the sealed enclosure 342. In one or more embodiments, the electronic device 330 can be disposed within the sealed enclosure 342. Further, in one or more embodiments, the enclosure 342 can be a hermetically-sealed enclosure.

Any suitable technique or combination of techniques can be utilized to attach the cover layer 340 to the first major surface 314 of the substrate 312. For example, in one or more embodiments, the cover layer 340 can be attached to the first major surface 314 of the substrate 312 by laser bonding the cover layer to the first major surface as is further described herein. In one or more embodiments, laser bonding the cover layer 340 can include forming a bond line in a region or at an interface between the first major surface 314 of the substrate 312 and the cover layer such that the bond line surrounds the cavity 318.

FIGS. 13A-H are schematic cross-section views of another embodiment of a method 700 for forming a sealed package 710. All of the design considerations and possibilities regarding the sealed package 10 of FIGS. 1-5 and the sealed package 310 of FIGS. 8A-I apply equally to the sealed package 710 of FIGS. 13A-H. In method 700, a substrate 712 is provided. A first major surface 714 and a second major surface 716 of the substrate 712 can be prepared by polishing to remove surface deformities such as burrs, gouges, ridges, or other irregularities. Different techniques may be used to polish the first major surface 714 and the second major surface 716. For example, surfaces 714, 716 can be mechanically polished, chemically polished, or treated by chemical-mechanical polishing (CMP) techniques. Surfaces 714, 716 can be polished until the surfaces exhibit comparatively low surface roughness values that enhance direct bond formation. Although surfaces 714, 716 may be polished to remove irregularities, the bonding process according to the present disclosure may not require the surfaces to be as smooth as surfaces used during typical wafer bonding techniques. Surfaces 714, 716 may be cleaned to remove particles and contaminates. Cleaning surfaces 714, 716 can include ultrasonic and/or megasonic cleaning.

In FIG. 13B, a cavity 718 can be formed in the first major surface 714 of the substrate 712. Any suitable technique or combination of techniques can be utilized to form the cavity 718, e.g., etching, ablation, laser-assisted etching, and combinations thereof. The cavity 718 includes a recessed surface 719. The recessed surface 719 can be polished using any suitable technique or combination of techniques, e.g., the techniques described herein utilized to polish the first and second major surfaces 714, 716 of the substrate 712.

In FIG. 13C, a conductive material layer 725 including a conductive sheet or foil as described in reference to FIGS. 8A-I can be disposed on the second major surface 716 of the substrate 712. The conductive material layer 725 can be attached to the second major surface 716 using any suitable technique or combination of techniques, e.g., forming a bond that hermetically seals the conductive layer to the second major surface. For example, electromagnetic radiation can be directed through one or both of the first major surface 714 of the substrate 712 and the recessed surface 719 and directed at an interface of the conductive material layer 725 and the second major surface 716 to form one or more bonds between the conductive material layer and the second major surface.

One or more portions of the conductive material layer 725 can be removed to form one or more external contacts 726 on the second major surface 716 as illustrated in FIG. 13D. Any suitable technique or combination of techniques can be utilized to form the external contacts 726, including, for example, photolithography, etching, laser ablation, etc. In one or more embodiments, a mask or masks can be formed on the second major surface 716, and the conductive material layer 725 can be formed over the mask. Portions of the conductive material layer 725 that are formed on the mask itself can be removed using any suitable technique or combination of techniques to form external contacts 726. In one or more embodiments, the bond formed when the conductive material layer 726 was attached to the substrate 712 remains between the external contact 726 and the second major surface 716 of the substrate 712 such that the contact is hermetically sealed to the outer surface. Any suitable technique or combination of techniques can be utilized to form external contacts 726.

As shown in FIG. 13E, one or more vias 722 can be formed through the substrate 712. Each via 722 can be formed such that it is within a closed shape or region defined by the bond such that the bond surrounds the via. Because the via 722 is within the shapes or regions formed by the bonds, the via 722 can be protected from the external environment. In one or more embodiments, an etch stop layer can be formed between the conductive material layer 725 and the second major surface 716 of the substrate 712 to prevent the formation of the via 722 from removing portions of the external contact 726.

Although not shown, one or more conductors can optionally be formed on the external contact 726 and/or on the second major surface 716 of the substrate 712. In one or more embodiments, one or more conductors can be electrically coupled to the external contact 726. Any suitable technique or combination of techniques can be utilized to form such conductors. In one or more embodiments, the conductors can be provided by forming a conductive material layer over the external contact 726 and the second major surface 716. This conductive material layer can then be patterned to form conductors in any desirable configuration.

As shown in FIG. 13F, conductive material 724 can be disposed in the via 722 to provide a conductive pathway from the external contact 726 to conductors, contacts, electronic devices, etc. disposed on the first-major-surface 714 side of the substrate 712, thereby providing feedthrough 720. Any suitable technique or combination of techniques can be utilized to form the conductive material 724 in the via 722. As mentioned herein, the via 722 can be substantially filled with the conductive material 724. In one or more embodiments, the conductive material 724 can be disposed on a portion or portions of one or more sidewalls of the vias as shown in FIG. 13F. Further, one or more conductors 750 can optionally be formed on the first major surface 714 of the substrate 712 either simultaneously with forming conductive material 724 in the vias 722 or sequentially. In one or more embodiments, the same material utilized for the conductive material 725 can also be utilized to form conductors 750. Conductors 750 can be formed using any suitable technique or combination of techniques. The optional conductors 750 described herein can be provided to, for example, electrically couple an electronic device or contact disposed on the first major surface 716 to the conductive material 724 in the via 722.

One or more electronic devices 730 can be disposed at least partially within the cavity 718 as shown in FIG. 13G. Electronic device 730 can include any suitable electronic device or devices. In one or more embodiments, the electronic device 730 can include a power source that can be at least partially disposed within the cavity 718 prior to attaching a cover layer 740 to the first major surface 714 of the substrate 712. The power source can be electrically connected to one or more electronic devices disposed within the cavity 718.

The electronic device 730 can be disposed at least partially within the cavity 718 such that a device contact 732 of the electronic device is electrically connected to the conductive material 724 in the via 722 either directly or through electrical connection to conductor 750. The electronic device 730 can include any suitable number of device contacts 732. The electronic device 730 can, therefore, be electrically connected to the external contact 726 when the device contact 732 is electrically connected to the conductive material 724 disposed within the via 722. In other words, an electrical pathway can be provided between the electronic device 730 and the second major surface 716 of the substrate 712 by electrically connecting the device to the feedthrough 720. In one or more embodiments, the device contact 732 can be electrically connected directly to the conductive material number 724 without an intervening internal contact or conductor 750 being present.

As shown in FIG. 13H, the cover layer 740 can be disposed over the cavity 718. The cover layer 740 can be attached to the first major surface 714 of the substrate 712 to form a sealed enclosure 742. In one or more embodiments, the electronic device 730 can be disposed within the sealed enclosure 742. Further, in one or more embodiments, the enclosure 742 can be a hermetically-sealed enclosure.

Any suitable technique or combination of techniques can be utilized to attach the cover layer 740 to the first major surface 714 of the substrate 712. For example, in one or more embodiments, the cover layer 740 can be attached to the first major surface 714 of the substrate 712 by laser bonding the cover layer to the first major surface as is further described herein. In one or more embodiments, laser bonding the cover layer 740 can include forming a bond line in a region or at an interface between the first major surface 714 of the substrate 712 and the cover layer such that the bond line surrounds the cavity 718.

Optionally, an insulative material (not shown) can be disposed within the cavity 718 such that the insulative material at least partially surrounds the electronic device 730. The insulative material, therefore, can be disposed within a sealed enclosure 742 that is formed by the cover layer 740 being disposed on the first major surface 714 of the substrate 712 as is further described herein. Any suitable insulative material or combination of materials can be disposed within the cavity 718 such that the insulative material at least partially surrounds the electronic device 730.

The various embodiments of sealed packages described herein can be utilized with any device or system that requires sealed conductive pathways between an exterior of the device to one or more electronic devices or components disposed within an interior of the package. For example, one or more embodiments of sealed packages described herein can be utilized with an implantable medical device or system. Nearly any implantable medical device or system employing leads may be used with the various embodiments of sealed packages described herein. Representative examples of such implantable medical devices include hearing implants, e.g., cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like.

Figure 9:
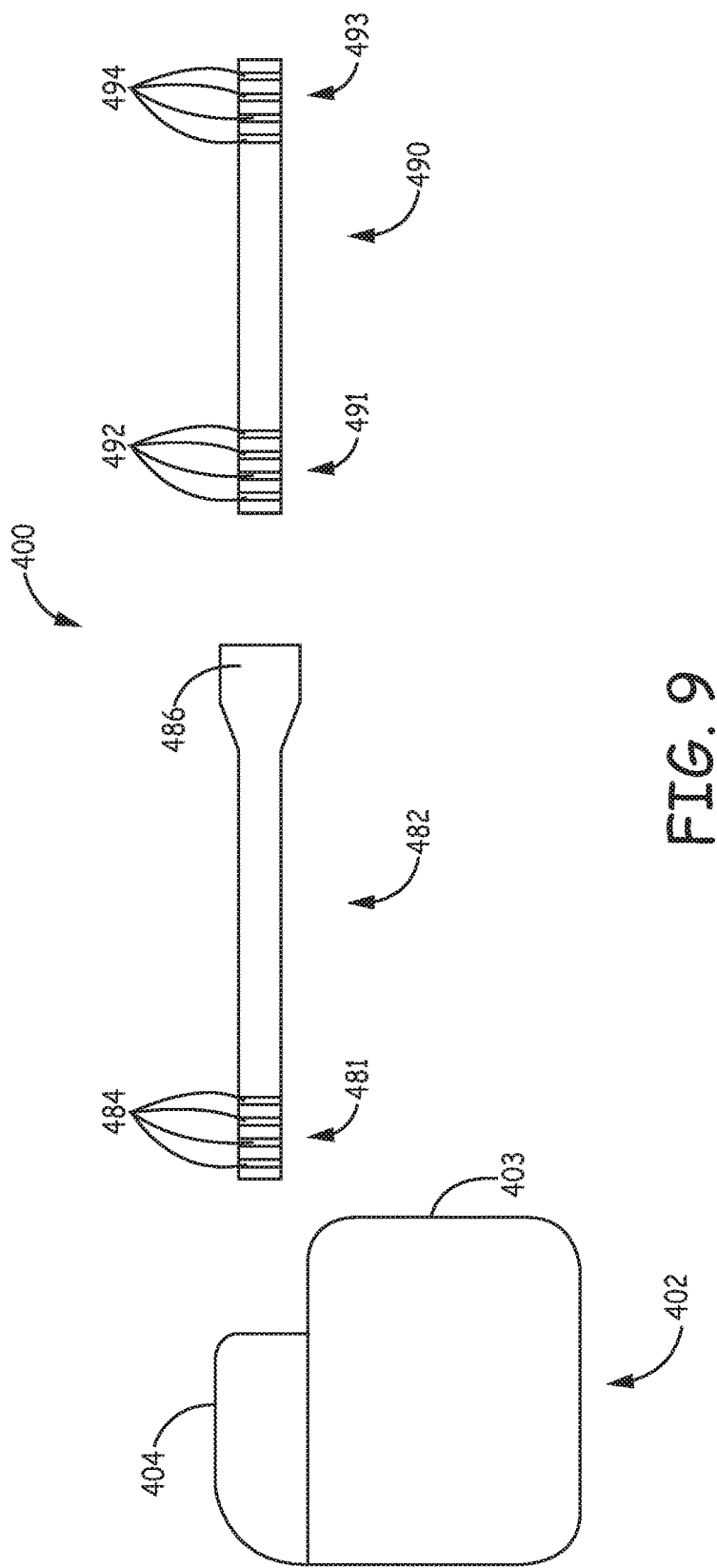
FIG. 9 is a schematic side view of one embodiment of an implantable medical device system.

For example, FIG. 9 is a schematic side view of one embodiment of an implantable medical device system 400. The system 400 includes an implantable medical device (IMD) 402, a lead 490, and a lead extension 482. In one or more embodiments, the system 400 can also include a sealed package (e.g., sealed package 10 of FIGS. 1-5).

The IMD 402 includes a connector header 404 adapted to receive a proximal portion 481 of the lead extension 482. A proximal portion 481 of lead extension 482 includes one or more electrical contacts 484 that are electrically coupled to internal contacts (not shown) at distal connector 486 of the lead extension. The connector header 404 of the IMD 402 includes internal contacts (not shown) and is adapted to receive the proximal portion 481 of the lead extension 482 such that the internal contacts of the connector header may be electrically coupled to the contacts 484 of the lead extension when the lead extension is inserted into the header.

The system 400 depicted in FIG. 9 further includes lead 490. The depicted lead 490 has a proximal portion 491 that includes contacts 492 and a distal portion 493 that includes electrodes 494. Each of the electrodes 494 can be electrically coupled to a discrete contact 492. The distal connector 486 of the lead extension 482 is adapted to receive the proximal portion 491 of the lead 490 such that the contacts 492 of the lead may be electrically coupled to the internal contacts of the connector of the extension. Accordingly, a signal generated by the IMD 402 can be transmitted to tissue of a patient by an electrode 494 of lead 490 when the lead is connected to the extension 482 and the extension is connected to the IMD. Alternatively or in addition, a signal received by electrode 494 of lead 490 from a patient may be transmitted to a contact of the IMD 402 when the lead is connected to the extension 482 and the extension is connected to the IMD.

It will be understood that lead 490 can be connected to IMD 402 without use of an extension 482. Any number of leads 490 or extensions 482 can be connected to device 402. While lead 490 is depicted as having four electrodes 494, it will be understood that the lead can include any number of electrodes, e.g. 1, 2, 3, 4, 5, 6, 7, 8, 16, 32, or 64 electrodes. Corresponding changes in the number of contacts 492 in lead 490, contacts 484 and internal contacts in connector 486 of lead extension, or internal contacts in header 404 of device 402 may be required or desired.

As used hereinafter, "lead" will refer to both "leads" and "lead extensions" unless the content and context clearly dictates otherwise.

Figure 10:
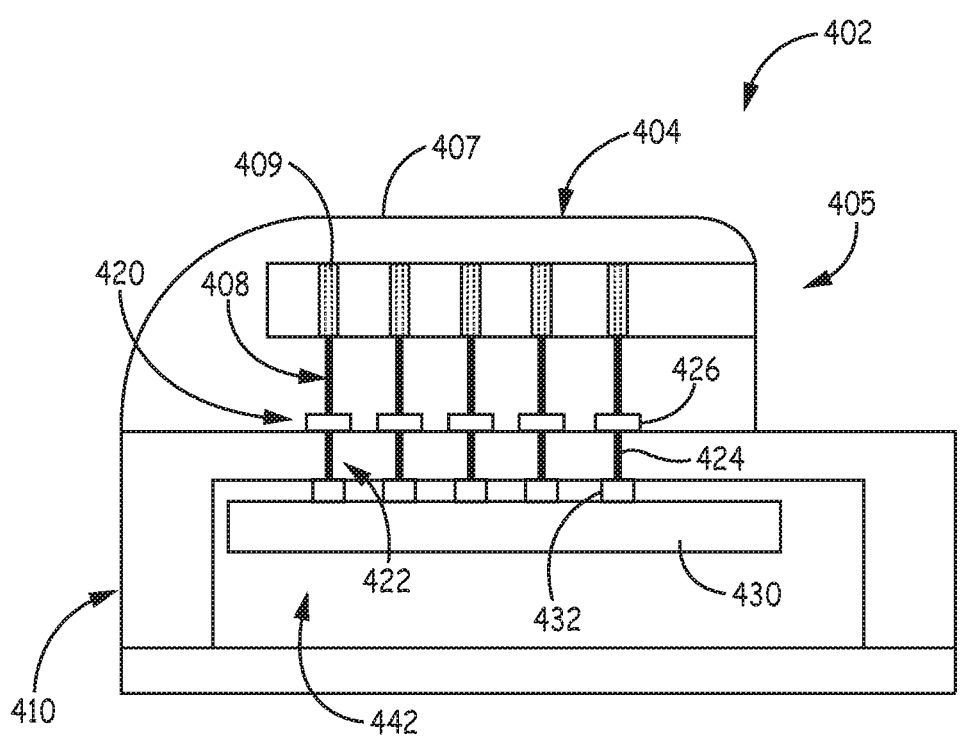
FIG. 10 is a schematic cross-section view of the implantable medical device of the system of FIG. 9.

FIG. 10 is a schematic cross-section view of the IMD 402 of FIG. 9. The IMD 402 further includes a sealed package 410 that includes one or more electronic devices 430 disposed within a sealed enclosure 442, and the connector header 404 disposed on or attached to the sealed package. The sealed package 410 can include any sealed package described herein, e.g., sealed package 10 of FIGS. 1-5. All of the design considerations and possibilities regarding the sealed package 10 of FIGS. 1-5 apply equally to the sealed package 410 of FIG. 10. A lead receptacle 405 is formed in a housing 407 of the header 404. The receptacle 405 is adapted to receive and electrically connect to contacts 484 of the lead extension 482 (or contacts 492 of the lead 490).

The receptacle 405 has internal contacts 409 positioned to align with and electrically couple with contacts 484 of the lead extension 482 and/or contacts 492 of the lead 490 when the lead extension or lead is properly inserted into the receptacle. The pitch of the internal contacts 409 of FIG. 10 is adapted to allow electrical connection between the contacts 484 of the lead extension 482 or contacts 492 of lead 490.

The electronic device 430 disposed within the sealed package 410 can be adapted to send electrical signals to a tissue of a patient, or receive signals from a tissue of a patient, through leads operably coupled to the electronics of the IMD 402. As used herein, the term "transmitted electrical signals" is used to refer to both the signals sent by the electronic device 430 to tissue of the patient or received by the electronics from the tissue of the patient. In one or more embodiments, the electronic device 430 can be electrically connected to internal contacts 409 of lead receptacle 405 via feedthroughs 420 of the sealed package 410. For example, in one or more embodiments, device contact 432 of the electronic device 430 can be electrically connected to conductive material 424 disposed within via 422. The device contact 432 can, therefore, be electrically connected to external contact 426 of feedthrough 420 through the conductive material 424 disposed in the via 422. The external contact 426 can in turn be electrically connected to the internal contact 409 of lead receptacle 405 by conductor 408. An electrical pathway is, therefore, formed between the internal contact 409 of lead receptacle 405 and electronic device 430.

In one or more embodiments, each conductor 408 can electrically couple an internal contact 409 of the lead receptacle 405 to a discrete channel of the electronic device 430. As used herein, a "channel" of the electronics is a discrete electronic pathway through which signals may be transmitted independently of another channel. The feedthroughs 420 can be electrically connected with internal contacts 409 via welding, soldering, brazing, coupling via conductive wires, or the like. Each channel of the electronics 406 can be independently connected with a discrete internal contact 409 of a receptacle, which can be coupled with a discrete contact 484 of the lead extension 482 or contact 492 of the lead 490, which can be coupled with a discrete electrode 494 of the lead. Accordingly, each channel of the electronics 406 can be operably coupled to a given electrode 494 of a lead.

Figure 11:
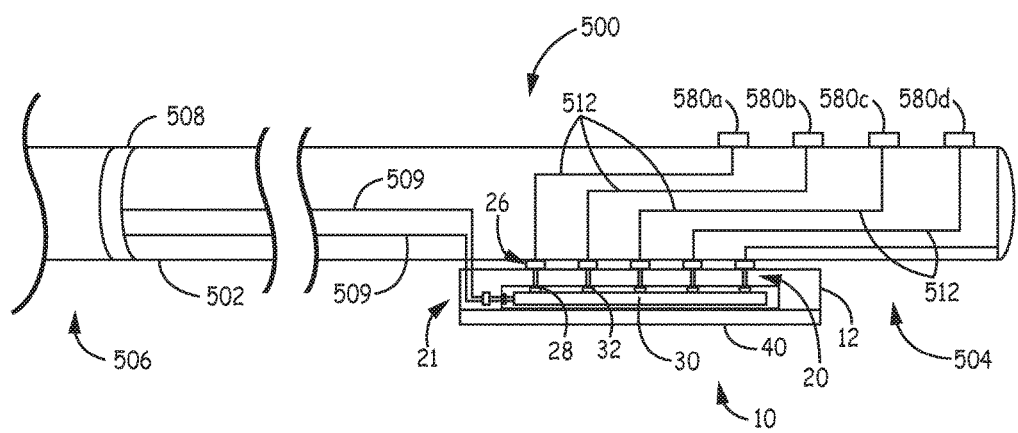
FIG. 11 is a schematic cross-section view of a lead that includes the sealed package of FIG. 1.

The various embodiments of hermetically-sealed packages described herein can be utilized with any system or device. For example, FIG. 11 is a schematic cross-section view of one embodiment of a lead 500. The lead 500 can be any suitable lead known in the art (e.g., lead 490 of implantable medical device 400 of FIGS. 9-10). All of the design considerations and possibilities regarding lead 490 (and lead extension 482) of FIG. 9 apply equally to lead 500 of FIG. 10. Further, the lead 500 can be utilized with any suitable external medical device or implantable medical device (e.g., implantable medical device 402 of system 400 of FIGS. 9-10). The lead 500 includes a lead body 502 that has a distal portion 504 and a proximal portion 506 that includes one or more contacts 508.

One difference between lead 500 and lead 490 is that lead 500 includes the sealed package 10 of FIGS. 1-5 disposed on or in the distal portion 504 of the lead body 502. Although the lead 500 is illustrated as including the package 10 of FIGS. 1-5, any sealed package can be utilized with the lead. In the embodiment illustrated in FIG. 11, the package 10 is coupled to a portion, e.g., the distal portion 504, of the lead body 502. The lead 500 optionally includes one or more output conductors 512 that are connected to the package 10. The one or more output conductors 512 can electrically connect the package 10 to electrodes 580a-d that are disposed on the lead 500. In one or more embodiments, the electronic device 30 can include a multiplexer that can be used for selective coupling of one or more of the electrodes 520a-d to one or more conductors or filers 509 as will be described in greater detail herein.

In one or more embodiments, the discrete contact 508 of the lead 500 can be electrically connected to the package 10 using any suitable technique or combination of techniques. In one or more embodiments, the discrete contact 508 of the lead 500 can be electrically connected to the package 10 through one or more conductors or filers 509 that are disposed on or within the lead body 502. The discrete contact 508 can be electrically connected to one or more of the feedthroughs 20 of the package 10 either directly or through the electronic device 30. For example, in one or more embodiments, the electronic device 30 can be a multiplexer that is electrically connected to one or more discrete contacts 508 of the lead and a feedthrough 21. Any suitable multiplexer can be utilized with the lead 500, e.g., the multiplexers described in co-owned U.S. Pat. No. 7,822,482 to Gerber. The electronic device 30 can be electrically connected to one or more discrete contacts 508 by a conductor or filer 509 that is disposed on or within the lead body 502 and is electrically connected to feedthrough 21 as shown in FIG. 11. The feedthrough 21 can be any suitable feedthrough described herein, e.g., feedthrough 20 of package 10. Further, any suitable technique or combination of techniques can be utilized to form the feedthrough 21 through one or both of the substrate 12 and the cover layer 40, e.g., the same techniques described for forming feedthrough 20 of package 10.

The feedthrough 21 can provide a sealed electrical pathway from the discrete contact 508 to the electronic device 30. Although one feedthrough 21 is illustrated as being formed through substrate 12 of package 10, any suitable number of feedthroughs can be formed through one or both of the substrate and the cover layer 40 to electrically connect any suitable number of contacts 508 to the electronic device 30.

The lead body 502 can include one or more conductors 509 that provide one or more inputs to the multiplexer 30. And the package 10 can include one or more conductors that provide one or more outputs from the electronic device 30 to the one or more feedthroughs 20. In one or more embodiments, outputs of the electronic device 30 can be directly connected to one or more internal contacts 28 of the package 10. In one or more embodiments, the number of outputs of the electronic device 30 corresponds to the number of external contacts 26, as there is one output for each external contact. Further, in one or more embodiments, the number of outputs is greater than the number of input conductors 509. The use of electronic device 30 within lead body 502 can reduce the number of input conductors 509 that extend along the entire length of the lead body.

With the electronic device 30 adjacent the distal portion 504 of the lead 500, the number of input conductors 509 that extend along substantially the entire length of lead body 502 can be reduced. For example, the input conductors 509 may include a chip power conductor, a chip ground conductor, a serial addressing conductor, a stimulation power conductor, and a stimulation return conductor return. The chip power and chip ground conductors can deliver operating power to the electronic device 30. The stimulation power and return conductors deliver stimulation pulses for application across a set of electrodes (e.g., electrodes 520a-d) in distal portion 504 of the lead 500, which, in the illustrated embodiment, are the external contacts 26 of the package 10. The serial addressing conductor carries a serial codeword that identifies a combination of external contacts 26 for application of stimulation pulses. Each of the electrodes 520a-d can be electrically coupled to the external contacts 26 directly or through one or more output conductors 512 as shown in FIG. 11. In response to the codeword, the electronic device 30 configures a switch matrix to direct the stimulation pulses across the specified combination of two or more external contacts 26. The codeword may be transmitted by pulse width modulation or other serial bus schemes, and may specify the external contacts 26 to be included in a contact combination, as well as the polarities of the contacts. In response to the address codeword, electronic device 30 applies the stimulation current across the specified set of external contacts 26.

In one or more embodiments, one or more therapeutic electrodes can be electrically connected to one or more external contacts 26 of the package 10. In one or more embodiments, one or more of the external contacts 26 can be connected to electrodes through conductors to provide electrical stimulation therapy to a patient or sense physiological signals, such as cardiac signs, from a patient.

Figure 12:
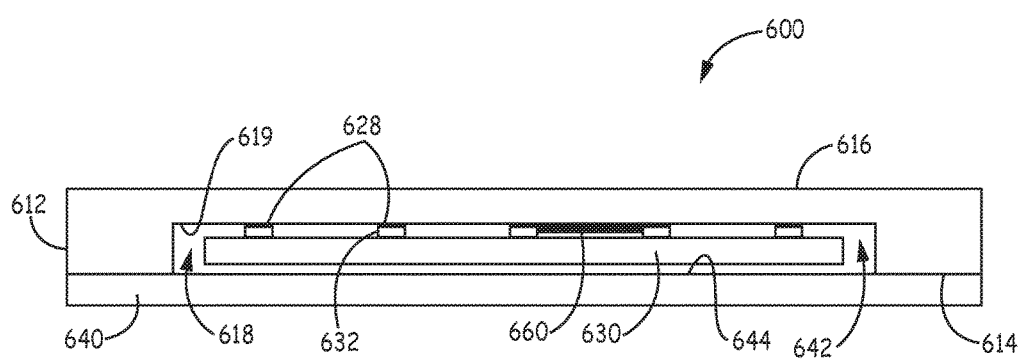
FIG. 12 is a schematic cross-section view of another embodiment of a sealed package.

Various embodiments of sealed packages described herein can include one or more feedthroughs that provide an electrical pathway from an external surface of the package to an enclosure within the package. In one or more embodiments, a sealed package does not require one or more feedthroughs but instead is contained completely within an enclosure of the package. For example, FIG. 12 is a schematic cross-section view of one embodiment of a sealed package 600. All of the design considerations and possibilities regarding the sealed package 10 of FIGS. 1-5 apply equally to the sealed package 600 of FIG. 12. Sealed package 600 includes a substrate 612 that includes a first major surface 614 and a second major surface 616. A cavity 618 can be disposed in the first major surface 614. The cavity can include a recessed surface 619. The package 600 also includes one or more internal contacts 628 disposed on the recessed surface 619 of the cavity 618. Electronic device 630 includes one or more device contacts 632. In one or more embodiments, one or more of the device contacts 632 can be electrically connected to one or more of the internal contacts 628 using any suitable technique or combination of techniques. The packaged 600 can also include a cover layer 640 disposed over the cavity 618 and attached to the first major surface 614 of the substrate 612 to form a sealed enclosure 642. In one or more embodiments, the electronic device 630 can be disposed within the sealed enclosure 642. Further, in one or more embodiments, the sealed enclosure 642 can be a hermetically-sealed enclosure. The package 600 can also include one or more conductors 660 disposed on one or both of the recessed surface 619 and an inner surface 644 of the cover layer 640. The one or more conductors 660 can electrically connect one or more of the internal contacts 628 together to form any suitable circuit or circuitry disposed within the sealed cavity 642. Although not shown, the sealed enclosure 642 can be at least partially filled with an insulative material to help protect the electronic device 630 from exposure to external environmental factors and to maintain the electronic device electrical connection with the internal contacts 628.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A hermetically-sealed package, comprising:
   a non-conductive substrate comprising a first major surface, a second major surface, and a cavity disposed in the first major surface, wherein the cavity comprises a recessed surface;
   a cover layer disposed over the cavity and attached to the first major surface of the non-conductive substrate to form a hermetically-sealed enclosure;
   a feedthrough comprising:
     a via between the recessed surface of the cavity and the second major surface of the substrate;
     a conductive material disposed in the via; and
     an external contact disposed over the via on the second major surface of the non-conductive substrate, wherein the external contact is electrically connected to the conductive material disposed in the via, and wherein the external contact is hermetically sealed to the second major surface of the non-conductive substrate by a laser bond surrounding the via;
   an electronic device disposed within the hermetically-sealed enclosure, wherein the electronic device comprises a device contact that is electrically connected to the conductive material disposed in the via such that the electronic device is electrically connected to the external contact; and
   a conductor disposed on the recessed surface and electrically connected to the electronic device.

2. The package of claim 1, further comprising an internal contact disposed over the via on the recessed surface of the cavity of the non-conductive substrate, wherein the internal contact is electrically connected to the conductive material in the via, and further wherein the device contact is electrically connected to the internal contact.

3. The package of claim 1, wherein the external contact is adapted to provide an electrical signal to tissue of a patient.

4. The package of claim 1, wherein the cover layer is hermetically sealed to the first major surface of the non-conductive substrate by a laser bond.

5. The package of claim 1, wherein the non-conductive substrate is substantially transmissive to light having a wavelength in a range of 200 nm to 30 µm.

6. The package of claim 1, further comprising a conductor disposed on the second major surface of the non-conductive substrate and electrically connected to the external contact.

7. The package of claim 1, wherein the cover layer comprises sapphire.

8. The package of claim 1, further comprising a power source disposed in the cavity and electrically connected to the electronic device.

9. An implantable medical device system that comprises a lead comprising a lead body and the hermetically-sealed package of claim 1 disposed in a distal portion of the lead body.

10. The implantable medical device system of claim 9, wherein the external contact of the hermetically-sealed package is electrically connected to a conductor of the lead.

11. A method of forming a hermetically-sealed package, comprising:
forming a cavity in a first major surface of a non-conductive substrate;
forming a via between a recessed surface of the cavity and a second major surface of the non-conductive substrate;
forming an external contact over the via on the second major surface of the non-conductive substrate;
disposing conductive material in the via such that the external contact is electrically connected to the conductive material in the via;
disposing an electronic device at least partially within the cavity such that a device contact of the electronic device is electrically connected to the conductive material in the via;
disposing a conductor on the recessed surface that is electrically connected to the electronic device;
disposing a cover layer over the cavity; and
attaching the cover layer to the first major surface of the non-conductive substrate to form a hermetically-sealed enclosure, wherein the electronic device is disposed within the hermetically-sealed enclosure.

12. The method of claim 11, wherein forming the cavity comprises etching the first major surface of the non-conductive substrate.

13. The method of claim 11, wherein forming the cavity comprises ablating the first major surface of the non-conductive substrate.

14. The method of claim 11, wherein forming an external contact comprises:
disposing a conductive layer on the second major surface over the via; and
removing a portion of the conductive layer to form the external contact over the via.

15. The method of claim 11, further comprising forming an internal contact on the recessed surface of the cavity over the via such that the internal contact is electrically connected to the conductive material in the via, wherein the device contact of the electronic device is electrically connected to the internal contact.

16. The method of claim 11, further comprising disposing an insulative material within the hermetically-sealed enclosure.

17. The method of claim 11, wherein attaching the cover layer comprises laser bonding the cover layer to the first major surface of the non-conductive substrate.

18. The method of claim 17, wherein laser bonding the cover layer comprises forming a bond line at an interface between the first major surface of the substrate and the cover layer such that the bond line surrounds the cavity.

19. The method of claim 11, further comprising:
disposing a power source at least partially within the cavity of the non-conductive substrate prior to attaching the cover layer to the first major surface of the non-conductive substrate; and
electrically connecting the power source to the electronic device.

20. A hermetically-sealed package, comprising:
a non-conductive substrate comprising a first major surface, a second major surface, and a cavity disposed in the first major surface, wherein the cavity comprises a recessed surface;
an internal contact disposed on the recessed surface of the cavity;
an electronic device comprising a device contact electrically connected to the internal contact;
a conductor disposed on the recessed surface and electrically connected to the electronic device; and
a cover layer disposed over the cavity and attached to the first major surface of the non-conductive substrate to form a hermetically-sealed enclosure, wherein the electronic device is disposed within the hermetically-sealed enclosure.

* * * * *